US012662664B2

(12) United States Patent
Burgard et al.

(10) Patent No.: US 12,662,664 B2
(45) Date of Patent: Jun. 23, 2026

(54) MODIFIED BACTERIAL HYALURONIDASE POLYPEPTIDE, PRODUCTION PROCESS, PHARMACEUTICAL COMPOSITIONS AND THEIR USES

(71) Applicant: PHARMACT HOLDING AG, Baar (CH)

(72) Inventors: Gunther Burgard, Homburg (DE); Rainer Boehnke, Berlin (DE); Sven Benson, Stuttgart (DE); Lenz Lorenz, Sindelfingen (DE); Philipp Schellenberger, Remshalden (DE)

(73) Assignee: PHARMACT HOLDING AG, Baar (CH)

( * ) Notice: Subject to any disclaimer, the term of this patent is extended or adjusted under 35 U.S.C. 154(b) by 375 days.

(21) Appl. No.: 17/920,348

(22) PCT Filed: Apr. 20, 2020

(86) PCT No.: PCT/EP2020/061025
§ 371 (c)(1),
(2) Date: Oct. 20, 2022

(87) PCT Pub. No.: WO2021/213623
PCT Pub. Date: Oct. 28, 2021

(65) Prior Publication Data
US 2023/0167428 A1 Jun. 1, 2023

(51) Int. Cl.
*C12N 9/26* (2006.01)
*C12N 15/70* (2006.01)

(52) U.S. Cl.
CPC ........... *C12N 9/2474* (2013.01); *C12N 15/70* (2013.01); *C12Y 402/02001* (2013.01)

(58) Field of Classification Search
CPC ........ C12N 9/2474; C12N 15/70; C12N 9/88; C12Y 402/02001; A61K 38/00; C07K 2319/21; C07K 2319/22
See application file for complete search history.

(56) References Cited

U.S. PATENT DOCUMENTS

| | | | | |
|---|---|---|---|---|
| 2008/0181892 A1* | 7/2008 | Ledbetter | ................ | A61P 31/00 424/134.1 |
| 2010/0003237 A1* | 1/2010 | Keller | ..................... | A61P 35/00 424/94.63 |
| 2010/0003238 A1* | 1/2010 | Frost | ....................... | A61P 35/04 424/94.62 |
| 2015/0010529 A1 | 1/2015 | Wei | ..................... | C12N 9/2474 |
| 2017/0218069 A1* | 8/2017 | Rosengren | ............. | A61K 47/60 |
| 2023/0321238 A1 | 10/2023 | Hu et al. | ............. | A61K 39/4631 |

FOREIGN PATENT DOCUMENTS

| | | | | |
|---|---|---|---|---|
| CN | 104263707 | 1/2015 | ............... | C12N 9/26 |
| EP | 2177227 | 4/2010 | ............. | A61K 38/47 |
| WO | 0077221 | 12/2000 | ............. | C12N 15/52 |
| WO | 2010077297 | 7/2010 | ............... | C12N 9/26 |
| WO | 2014165713 | 10/2014 | ........ | A61K 31/7008 |
| WO | 2016033555 | 3/2016 | ............. | C07K 16/28 |
| WO | 2019028186 | 2/2019 | ............... | A61K 8/14 |
| WO | 2019195310 | 10/2019 | ............. | C07K 14/74 |
| WO | 2020038490 | 2/2020 | ........... | A61K 35/761 |

OTHER PUBLICATIONS

Berry AM, et al. Cloning and nucleotide sequence of the Streptococcus pneumoniae hyaluronidase gene and purification of the enzyme from recombinant *Escherichia coli*. Infect Immun. Mar. 1994;62(3):1101-8. doi: 10.1128/iai.62.3.1101-1108.1994. PMID: 8112843; PMCID: PMC186229. (Year: 1994).*

Gupta S (2003). Project Report Codon Optimization. Plant and Molecular Biology Department, Arizona State University. (Year: 2003).*

Gustafsson C, Govindarajan S, Minshull J. Codon bias and heterologous protein expression. Trends Biotechnol. Jul. 2004;22(7):346-53. doi: 10.1016/j.tibtech.2004.04.006. PMID: 15245907. (Year: 2004).*

International Search Report and Written Opinion issued in PCT/EP2020/061025, dated Nov. 13, 2020, 12 pages.

International Preliminary Report on Patentability issued in PCT/EP2020/061025, dated Oct. 25, 2022, 7 pages.

Ferrer et al., "A Novel Hyaluronidase from Brown Spider (*Loxosceles intermedia*) Venom (Dietrich's Hyaluronidase): From Cloning to Functional Characterization" *PLOS Neglected Tropical Diseases*, vol. 7, Issue 5, May 2, 2013, 12 pages.

Messina, et al., "Identification and characterization of bacterial hyaluronidase and its production in a recombinant form" *FEBS Letters*, vol. 590, No. 14, Jul. 4, 2016, 10 pages.

Jedrzejas et al., "Expression and Purification of *Streptococcus pneumoniae* Hyaluronate Lyase from *Escherichia coli*", Sep. 1997, 7 pages.

Tomoyasu Aizawa, "Ni-NTA affinity column" Protein Science Society Archive #019, May 2008, with Machine English translation, 22 pages.

* cited by examiner

*Primary Examiner* — Sharmila G Landau
*Assistant Examiner* — Natalie Iannuzo
(74) *Attorney, Agent, or Firm* — HAYES SOLOWAY P.C.

(57) ABSTRACT

Disclosed is a modified bacterial hyaluronidase polypeptide, a production process thereof, and a pharmaceutical composition containing the modified bacterial hyaluronidase polypeptide, and its uses.

11 Claims, 3 Drawing Sheets
(3 of 3 Drawing Sheet(s) Filed in Color)
Specification includes a Sequence Listing.

MODIFIED BACTERIAL HYALURONIDASE POLYPEPTIDE, PRODUCTION PROCESS, PHARMACEUTICAL COMPOSITIONS AND THEIR USES

TECHNICAL FIELD

The present invention relates to a modified bacterial hyaluronidase polypeptide, a production process thereof, a pharmaceutical composition comprising the inventive modified bacterial hyaluronidase polypeptide and its uses.

PRIOR ART

Hyaluronic acid is an essential component of the extracellular matrix and a quantitatively significant constituent of the interstitial barrier. Hyaluronidase is a hydrolytic enzyme that cleaves hyaluronic acid in D-glucuronic acid and N-acetyl glucosamine, increasing the permeability of the interstitial matrix. Hyaluronidase is widely distributed in nature. In the human, six different hyaluronidases, HYAL1-4, HYAL-P1 and PH-20, have been identified, wherein PH-20 is regarded to exert the strongest biologic activity.

Today, animal-derived bovine or ovine testicular hyaluronidases as well as synthetic hyaluronidases are clinically applied as adjuncts to increase the bioavailability of drugs, for the therapy of extravasations, or for the management of complications associated with the aesthetic injection of hyaluronic acid-based fillers.

While hyaluronidase derived from animal origin imparts a risk of transmitting animal diseases, such spongiform encephalopathy, human and bacterial recombinant hyaluronidase exhibit a higher purity, which reduces pharmaceutical risks.

In order to meet the clinical need, it is an aim of the present invention to provide a hyaluronidase polypeptide that is suitable for pharmaceutical application and in particular exhibits a suitable high purity degree, and/or a suitable specific activity, suitable stability and solubility and at the same time exhibits a time and cost effective production process.

BRIEF DESCRIPTION OF THE INVENTION

The aforementioned aim is solved at least in part by means of the claimed inventive subject matter. Advantages (preferred embodiments) are set out in the detailed description hereinafter and/or the accompanying figures as well as in the dependent claims.

Accordingly, a first aspect of the invention relates to a modified bacterial hyaluronidase polypeptide comprising or consisting of at least 90% sequence identity to SEQ ID No. 1, characterized in that the hyaluronidase polypeptide comprises a C-terminal HIS tag of SEQ ID No. 7 and an N-terminal Strep tag of SEQ ID No. 5.

A second aspect of the invention relates to a nucleic acid encoding the inventive modified bacterial hyaluronidase polypeptide, preferably wherein the nucleic acid comprises or consists of SEQ ID No. 2.

A third aspect of the invention relates to a recombinant expression vector comprising a vector and the inventive nucleic acid.

A fourth aspect of the invention relates to a host cell transformed with the inventive recombinant expression vector, preferably wherein the host cell is *E. coli*.

A fifth aspect of the invention relates to a process of production of a purified bacterial hyaluronidase polypeptide comprising or consisting of the following steps:

a. Culturing a transformed inventive host cell in a suitable growth medium under suitable growth conditions to express the inventive bacterial hyaluronidase polypeptide, b. Harvesting the cultured transformed host cell of step a), c. Lysing the harvested host cells of step b) and separating resulting host cell fragments from resulting host cell content comprising the inventive bacterial hyaluronidase polypeptide, and d. Purifying the resulting host cell content of step c) with HIS affinity chromatography and STREP affinity chromatography to result in the inventive purified bacterial hyaluronidase polypeptide.

A sixth aspect of the invention relates to a modified bacterial hyaluronidase polypeptide comprising or consisting of at least 90% sequence identity of SEQ ID No. 1 obtainable according to the inventive production process.

A seventh aspect of the invention relates to a pharmaceutical composition comprising the inventive modified bacterial hyaluronidase polypeptide in a therapeutically effective amount and one or more pharmaceutically acceptable excipients.

An eighth aspect of the invention relates to a method of treating a hyaluronan-associated and/or proteoglycan-associated disease or disorder, preferably selected from a group consisting of homozygous familial hypercholesterolemia (xanthomatose), heterozygous familial hypercholesterolemia or diabetic foot syndrome, comprising administering the inventive modified bacterial hyaluronidase polypeptide or the inventive pharmaceutical composition to a subject in need thereof.

The inventive aspects of the present invention as disclosed hereinbefore can comprise any possible (sub-)combination of the preferred inventive embodiments thereof as set out in the dependent claims or as disclosed in the following detailed description and/or in the accompanying figures, provided the resulting combination of features is reasonable to a person skilled in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further characteristics and advantages of the present invention will ensue from the accompanying drawings, wherein.

DETAILED DESCRIPTION OF THE INVENTION

Figure 1:
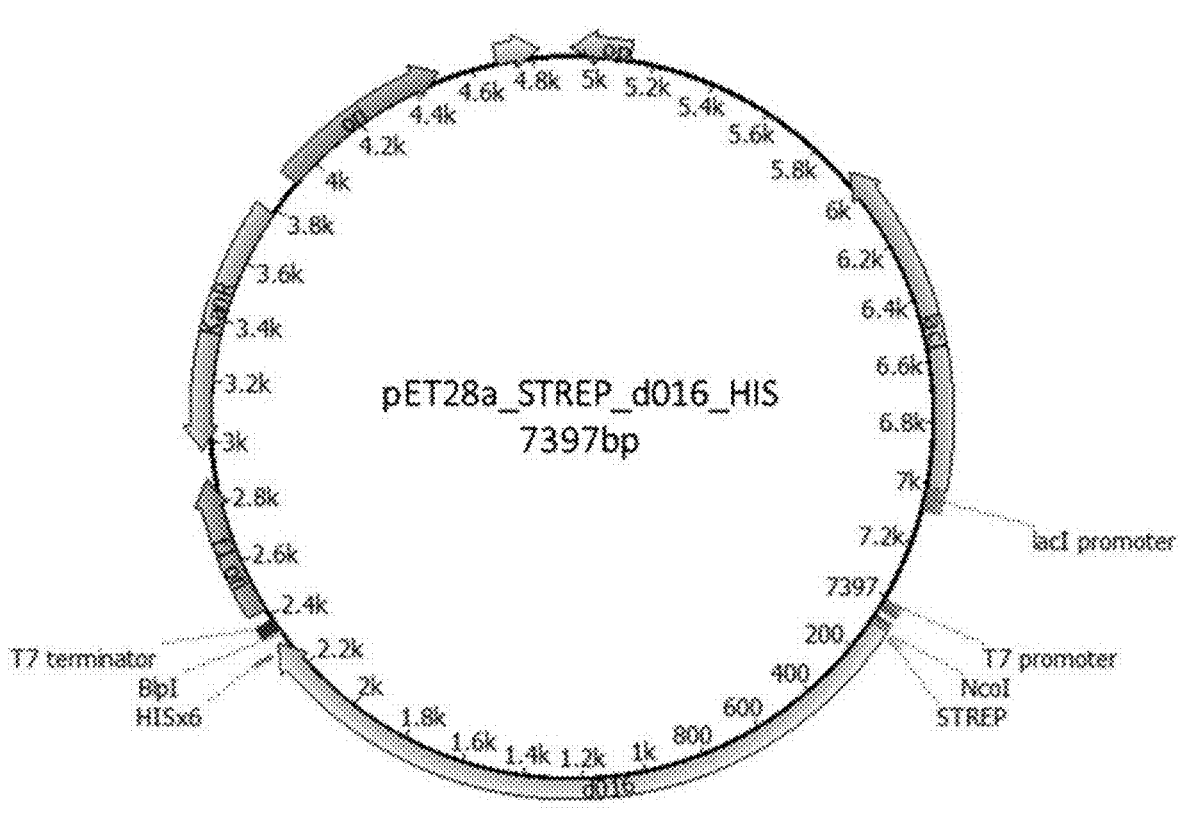
FIG. 1 represents a Vector Map plasmid of an inventive recombinant expression vector.

As set out in more detail hereinafter, the inventors of the different aspects of the present invention have found out that the inventive modified bacterial hyaluronidase polypeptide comprising or consisting of at least 90% sequence identity to SEQ ID No. 1, characterized in that the hyaluronidase polypeptide comprises a C-terminal HIS tag of SEQ ID No. 7 and an N-terminal Strep tag of SEQ ID No. 5, exhibits a high purity of >98.8% (see example section 1.4.1) and a high Specific Activity of 1,500,000 U/mg (see example section 1.4.2).

In contrast thereto, comparative hyaluronidases, such as bovine hyaluronidases exhibit a wide range of lower Specific Activities, namely in the range of 300 to 15,000 U/mg (see example section 2.3). PH20, regarded as the most active out of the human hyaluronidases, also exhibits a lower Specific Activity, namely in the range of 40,000 and 50,000 U/mg. The Specific Activity of bacterial hyaluronidase derived from *Streptomyces koganeiensis* is comparable to the Specific Activity of PH20 and, thus, is also lower than the Specific Activity of the inventive modified bacterial hyaluronidase.

Moreover, the inventive modified bacterial hyaluronidase exhibits suitable stability and solubility, which is shown in example section 1.4.5 below. The increased stability, including stability against (exo-)peptidases (half life) may be due to the use of the respective C-terminal HIS tag of SEQ ID No. 7 and the respective N-terminal Strep tag of SEQ ID No. 5. The respective tags may also increase the solubility of the inventive modified bacterial hyaluronidase in comparison to the wild-type hyaluronidase (see SEQ ID No. 3, DNA encoding wild-type hyaluronidase see SEQ ID. No. 4). Due to the increased stability and solubility properties, the inventive modified bacterial hyaluronidase is preferred for formulating pharmaceutical compositions, in particular parenteral injection compositions.

Thus, the inventive production process for providing a purified modified bacterial hyaluronidase provides a comparatively high yield and at the same time, a high purity and high Specific Activity already in laboratory scale and is in view of the production steps time and cost effective.

In the context of the present invention, the expression "inventive modified bacterial hyaluronidase polypeptide comprising or consisting of at least 90% sequence identity to SEQ ID No. 1, characterized in that the hyaluronidase polypeptide comprises a C-terminal HIS tag of SEQ ID No. 7 and an N-terminal Strep tag of SEQ ID No. 5" is synonymously used to "inventive bacterial hyaluronidase polypeptide", "inventive bacterial hyaluronidase", or "inventive hyaluronidase", wherein the expressions mean that the inventive hyaluronidase comprises at least 90, 91, 92, 93, 94, 95, 96, 97, 98, 99, 99.5, of the sequence of SEQ ID No. 1 or that it consists of 100% of SEQ ID No. 1 and that the inventive hyaluronidase at the same time exhibits the C-terminal HIS tag of SEQ ID. No. 7 and the N-terminal Strep tag of SEQ ID No. 5. In case that the sequence of the inventive hyaluronidase consists of 100% of the SEQ ID No. 1, the inventive hyaluronidase is also synonymously called "d016".

Thus, the inventive modified bacterial hyaluronidase, preferably d016, is suitable for use in a pharmaceutical composition.

In view of the presented comparatively high Specific Activity, purity, stability, solubility and safety profiles, the inventive modified bacterial hyaluronidase, preferably d016 is suitable for use in the treatment or prophylaxis of a hyaluronan-associated and/or proteoglycan-associated disease or disorder. The inventors have found out that the inventive modified bacterial hyaluronidase, preferably d016, is in particular suitable for use in the treatment or prophylaxis of homozygous familial hypercholesterolemia (xanthomatose), heterozygous familial hypercholesterolemia or diabetic foot syndrome.

Homozygous familial hypercholesterolemia (HoFH) is an inherited rare disease with a prevalence of 1 in 1,000,000. As a form of familial hypercholesterolemia, it is a lipid metabolism disorder. Patients with HoFH stand out due to a massive increase in low-density lipoprotein (LDL), a cholesterol fraction in the blood, with deposits in the skin and tendons, the so-called xanthomas (yellowish, nodular deposits of lipids). The lipid is also deposited in the vessel walls and causes early onset of severe atherosclerosis with a significantly reduced life expectancy. Patients suffer their first heart attack in early childhood, already from the age of about 5 years, have to undergo lipid apheresis weekly, receive concomitant medication in highest doses, and yet unfortunately have a life expectancy of only about 30 years on average.

HoFH is to be distinguished from the much more frequent heterozygous familial hypercholesterolemia (HeFH), which is also associated with a significantly increased risk of early cardiovascular events, but is less dramatic. The prevalence of this hereditary disease is estimated at 1:200 to 1:500. Here, too, signs of arteriosclerosis, i.e. diseases and symptoms caused by vascular disease, e.g. peripheral arterial occlusive disease, narrowing of the coronary arteries up to heart attack, stroke, can occur at a young age, but later and to a lesser extent than in the homozygous variant of the disease.

The inventive bacterial hyaluronidase is effective in the treatment and/or prophylaxis of HoFH and HeFH in view of its reducing effect on the tissue Extra Cellular Matrix (ECM) and chondroitin-6-sulfate and other proteoglycan levels in the atherosclerotic plaques and in the arteriosclerotic vessel walls. The administration of a therapeutically effective amount of the inventive modified bacterial hyaluronidase, preferably d016, thus leads to a size reduction of the stenosing plaques and an increase in the elasticity of the vascular wall.

Diabetic foot syndrome (DFS) is a syndrome of pathological changes based on painless sensory neuropathy and/or peripheral arterial occlusive disease (PAVK) in diabetes mellitus. It is most common in patients with type 2 diabetes mellitus and is associated with a high risk of poorly healing wounds on the foot. About 15% of diabetics develop painless (due to sensory neuropathy), poorly healing wounds on the feet in the course of their lives. Every year, about 4% of diabetics develop a new wound, and 0.1% develop a so-called Charcot foot due to the collapse of the arch of the foot.

In view of the PAVK aspect of the diabetic foot syndrome, the inventive bacterial hyaluronidase is effective in the treatment and/or prophylaxis of the diabetic foot syndrome by exhibiting a reducing effect on the tissue Extra Cellular Matrix (ECM) and chondroitin-6-sulfate and other proteoglycan levels in the atherosclerotic plaques and in the arteriosclerotic vessel walls. Thus, it leads to a size reduction of the stenosing plaques and an increase in the elasticity of the vascular wall. In addition, the inventive bacterial hyaluronidase has an effect on the neuropathic aspect of the diabetic foot syndrome. In this regard, it reduces the increased hyaluronic acid concentrations present in the nerve sheath regions caused by chronic polyneuritis. The associated nerve transmission disorder based on disturbed isolation function of the myelin sheaths is reduced and the nerve transmission ability is increased again.

In addition, the present invention provides as second aspect a nucleic acid encoding the inventive modified bacterial hyaluronidase polypeptide of the first aspect. All features and embodiments disclosed with respect to the first aspect of the present invention are combinable alone or in (sub-)combination with the second aspect of the present invention including each of the preferred embodiments thereof, provided the resulting combination of features is reasonable to a person skilled in the art.

According to a preferred embodiment of the second inventive aspect, the nucleic acid comprises or consists of SEQ ID No. 2. The nucleic acid sequence encoding the C-terminal HIS tag of the inventive hyaluronidase is preferably SEQ ID No. 8 and the nucleic acid sequence encoding the N-terminal Strep tag of the inventive hyaluronidase is preferably SEQ ID No. 6. The inventive nucleic acid may be prepared according to any suitable method. An example method is described in the example section 1.1.1 below.

In the context of the present invention, the expression "inventive nucleic acid" refers to a nucleic acid encoding the inventive modified bacterial hyaluronidase, preferably d016. The inventive nucleic acid preferably comprises or consists of at least 90% sequence identity to SEQ ID. 2, preferably the inventive nucleic acid consists of 100% SEQ ID No. 2.

According to a third aspect of the present invention, a recombinant expression vector comprising the inventive nucleic acid of the second aspect. All features and embodiments disclosed with respect to the first or second aspect of the present invention are combinable alone or in (sub-) combination with the third aspect of the present invention including each of the preferred embodiments thereof, provided the resulting combination of features is reasonable to a person skilled in the art.

The inventive recombinant expression vector of the third aspect may be prepared according to any suitable method. An example method is described in example section 1.1.1 below. The inventive recombinant expression vector comprises the inventive nucleic acid comprising or consisting of SEQ ID No. 2, any suitable vector, such as a pET-28a DNA vector, in particular pET28a using NcoI/BlpI restriction sites. The inventive recombinant expression vector may be of any suitable form, such as in form of a plasmid.

According to a fourth aspect of the present invention, a host cell transformed with the inventive recombinant expression vector of the third aspect is provided. All features and embodiments disclosed with respect to the first to third aspect of the present invention are combinable alone or in (sub-)combination with the fourth aspect of the present invention including each of the preferred embodiments thereof, provided the resulting combination of features is reasonable to a person skilled in the art.

The inventive host cell of the fourth aspect may be prepared according to any suitable method. An example method is described in example section 1.1.2 below. The inventive host cell may be selected from any suitable host cells. Preferably, the host cell is selected from *E. coli* cells, more preferably *E. coli* BL21 (DE3) competent cells, which provide a comparatively high yield of inventive modified bacterial hyaluronidase, preferably d016.

The fifth aspect of the present invention provides a process of production of a purified bacterial hyaluronidase polypeptide according to the first inventive aspect. All features and embodiments disclosed with respect to the first to fourth aspects of the present invention are combinable alone or in (sub-)combination with the fifth aspect of the present invention including each of the preferred embodiments thereof, provided the resulting combination of features is reasonable to a person skilled in the art.

The inventive production process can be conducted in laboratory scale using conventional shaker flasks or may be up-scaled for use in a fermenter. In view of up-scaling to fermenter production, the process steps may be optimized in view of high density growth, onset/offset of expression, mixing speed and time, and applicable temperature. The inventors found out that in view of the high specific activity of the inventive modified bacterial hyaluronidase, preferably d016, already the laboratory scale using shaker flasks is sufficient to produce a meaningful amount (yearly amount) of the inventive modified bacterial hyaluronidase, preferably d016, for use in the treatment and/or prophylaxis of homozygous familial hypercholesterolemia (xanthomatose), heterozygous familial hypercholesterolemia or diabetic foot syndrome.

The inventive production process of the fifth aspect comprises or consists of the following steps:

Step a) Culturing a transformed host cell according to the fourth inventive aspect in a suitable growth medium under suitable growth conditions to express the inventive modified bacterial hyaluronidase polypeptide according to the first inventive aspect. As an example, terrific broth (TB) media can be used. The respective broth media may be supplemented by suitable antibiotics, such as kanamycin, and/or buffer constituents, such as potassium phosphate buffer. The growth media also comprises a suitable expression inducer, such as Isopropyl β-D-1-thiogalactopyranoside (IPTG). According to laboratory scale, cell growth and protein expression may be conducted in a shaker culture flask at a suitable temperature, preferably at 28 to 30° C. and shaking, preferably 180 rpm, for 18 to 20 hours.

Step b) Harvesting the cultured transformed host cell of step a). After culturing the transformed host cells under suitable growth conditions, the host cells are harvested with suitable methods. According to laboratory scale, preferably pyrogen-free, sterile tubes are used to collect the harvested host cell containing growth media. This harvested growth medium is preferably centrifuged, preferably at 4 000 rcf at a reduced temperature, preferably 4° C., for at least 30 minutes in order to separate the medium from the host cells, which aggregate to so called pellets after centrifugation. The supernatant is to be discarded and the harvesting tubes are preferably sealed and stored at reduced temperature, preferably below 0° C., more preferably at −80° C.

Step c) Lysing the harvested host cells of step b) and separating resulting host cell fragments from resulting host cell content comprising the inventive bacterial hyaluronidase polypeptide. According to laboratory scale, the host cells, which after centrifugation form aggregated pellets, are generally resuspended and mixed, preferably by vortexing, in suitable medium, preferably a suitable buffer medium, such as phosphate buffered saline (PBS; containing 280 mM NaCl, 6 mM KCl, 15.1 mM $Na_2HPO_4$, 4.9 mM $NaH_2PO_4$, pH=7.4 at room temperature). The host cells are lysed by any suitable methods, such as sonication. In order to maintain suitable temperatures within the medium, the sonication takes preferably place at reduced temperatures, more preferably wherein the tubes are surrounded by ice while sonicating the medium. The resulting host cell fragments are separated from the inventive bacterial hyaluronidase polypeptide with suitable methods, preferably by centrifugation, more preferably centrifugation at reduced temperature, e.g. 4° C., for at least 30 minutes at e.g. 4 000 rcf. The supernatant comprising the inventive bacterial hyaluronidase is preferably transferred to a new tube and optionally one or more centrifugation steps are further conducted. The resulting supernatant comprising the inventive bacterial hyaluronidase is then used for the purification step d).

Step d) Purifying the resulting host cell content of step c) with HIS affinity chromatography and STREP affinity chromatography to result in a purified inventive bacterial hyaluronidase polypeptide of the first aspect. Preferably the HIS- and STREP affinity chromatography takes place subsequently, wherein the order is interchangeable, i.e. wherein the HIS affinity chromatography purification is conducted first followed by STREP affinity chromatography or vice versa. In the following the subsequent purification conducting first HIS affinity chromatography and then STREP affinity chromatography is described as one example embodiment. In view that HIS affinity chromatography columns are generally cheaper than STREP affinity chromatography columns, the high purity yield may be achieved in a more cost effective way in case the HIS affinity chromatography is conducted first.

According to the present invention, any suitable HIS affinity chromatography can be used in order to bind to the C-terminal HIS tag (amino acids 735 to 740 of SEQ ID NO. 1, see also SEQ ID NO. 7) of the inventive modified bacterial hyaluronidase. According to laboratory scale, as an example one or more suitable gravitational HIS-purification columns are equilibrated to general PBS downstream buffer. The content of each tube resulting after step c) is distributed to the one or more HIS-columns. Optionally the HIS purification procedure is repeated one, two or more times, preferably two times. The loaded one or more HIS-columns are then preferably washed with a suitable washing medium, e.g. with 10 mM imidazole PBS solution, before being eluted in a suitable eluting medium, e.g. 150 mM imidazole PBS solution. Generally, the eluate of the one or more HIS-columns originating from the same production flask (tube) are combined and preferably diluted to 35 ml with general downstream buffer PBS. Preferably, the purified eluate samples comprising the inventive modified bacterial hyaluronidase is then stored under reduced temperature, preferably on ice until the following STREP purification.

According to the present invention, any suitable STREP affinity chromatography can be used in order to bind to the N-terminal STREP tag (amino acids 3 to 10 of SEQ ID NO. 1, see also SEQ ID NO. 5) of the inventive modified bacterial hyaluronidase. According to laboratory scale, one or more suitable syringe-based STREP affinity chromatographic columns can preferably be used. As an example, one or more syringe-based STREP-purification steps, more preferably with a flowrate <5 ml/min, are performed. STREP-columns (5 ml bed volume) are generally washed and equilibrated with 2×25 ml general downstream buffer PBS. A suitable amount of the eluate sample resulting from the HIS purification is applied and runs through the STREP column. The loaded STREP column is then preferably washed with a suitable amount of general downstream PBS buffer to remove any remaining contaminant proteins. By applying a suitable eluting medium, e.g. 2.5 mM d-Desthiobiotin containing PBS buffer, the protein of interest, namely the inventive modified bacterial hyaluronidase, is eluted, preferably into a fresh, sterile and pyrogen-free tube. This tube is either stored at reduced temperature, e.g. on ice, or the lyophilized to result in a dry storable product of the purified inventive modified bacterial hyaluronidase. The STREP column can be reused after suitable regeneration according to the prior art.

Optionally, the buffer of the eluate may be exchanged by suitable methods including centrifugation of the eluate to aggregate the inventive bacterial hyaluronidase, discarding the supernatant and resuspending the aggregated inventive bacterial hyaluronidase into a different buffer medium, such as Tris-HCL NaCl. According to a preferred embodiment the resuspended inventive bacterial hyaluronidase is stored under reduced temperature, e.g. on ice for further post processing, such as polishing.

According to a preferred embodiment, the inventive purification step additionally comprises one or more suitable polishing steps to remove last impurities of the inventive bacterial hyaluronidase polypeptide in step d) and, thus, to increase purity thereof. According to laboratory scale, one or more endotoxin removal steps, such as Polymyxin B based endotoxin removal steps; one or more sterile filtration steps, and one or more particle removal steps can be performed.

According to the present invention, the laboratory scale protein yield results in 0.09 to 0.13 mg/ml after HIS purification and 0.04 to 0.06 mg/ml after dual HIS/STREP purification and subsequent polishing purification step (see example section item 1.3.4 below). It is expected that this yield significantly increases upon fermentation scale production.

According to the sixth aspect of the present invention, a modified bacterial hyaluronidase polypeptide, preferably wherein the inventive modified bacterial hyaluronidase polypeptide consists of SEQ ID No. 1, obtainable according to the inventive production process according to the fifth aspect is provided. All features and embodiments disclosed with respect to the first to fifth aspect of the present invention are combinable alone or in (sub-)combination with the sixth aspect of the present invention including each of the preferred embodiments thereof, provided the resulting combination of features is reasonable to a person skilled in the art.

According to a seventh aspect of the present invention, a pharmaceutical composition comprising the inventive modified bacterial hyaluronidase polypeptide according to the first or sixth aspect of the present invention in a therapeutically effective amount and one or more pharmaceutically acceptable excipients is provided. All features and embodiments disclosed with respect to the first to sixth aspect of the present invention are combinable alone or in (sub-)combination with the seventh aspect of the present invention including each of the preferred embodiments thereof, provided the resulting combination of features is reasonable to a person skilled in the art.

In general, the therapeutically effective amount of the inventive bacterial hyaluronidase depends on the therapeutic application of the pharmaceutical composition. According to the present invention, the term "therapeutically active amount" means that the amount of inventive modified bacterial hyaluronidase polypeptide, preferably wherein the amount of the inventive modified bacterial hyaluronidase polypeptide consisting of SEQ ID No. 1, in the pharmaceutical composition or in a pharmaceutical unit dose thereof is suitable for treatment or prophylaxis of a hyaluronan-associated and/or proteoglycan-associated disease or disorder, preferably selected from a group consisting of homozygous familial hypercholesterolemia (xanthomatose), heterozygous familial hypercholesterolemia, or diabetic foot syndrome.

As an example, in case the pharmaceutical composition is a parenteral liquid composition for intravenous application, the inventive bacterial hyaluronidase may be provided as a concentrate in a vial with 1 to 10, preferably 2 or 5 mL in a therapeutically effective amount between 15,000 to 1,500,000 U/mL. According to a preferred embodiment, the unit dose of the inventive pharmaceutical composition comprises the inventive modified bacterial hyaluronidase polypeptide in a concentration range of 200 U per kg/per day to 30,000 U per kg/per day. In order to increase the half-life of the inventive bacterial hyaluronidase, the dosing scheme may preferably comprise a suitable bolus amount of the inventive hyaluronidase in order to saturate the exo- and/or endo-proteinases followed by a subsequent administration of the therapeutically effective unit dose amount. Preferably, in case of intravenous administration, the subsequent unit dose is administered up to 1 hour, alternatively up to 30 minutes or up to 15 minutes or up to 5 minutes after the bolus administration of the inventive bacterial hyaluronidase.

Notwithstanding the aforementioned, the inventive pharmaceutical composition can be present in any suitable application form, such as solid, semi-solid or liquid application form. The therapeutically effective amount is to be calculated accordingly. As an example, the solid form of inventive pharmaceutical composition may be presented as dried or lyophilized form. In addition to the inventive bacterial hyaluronidase polypeptide, one or more pharmaceutically acceptable excipients, such as one or more constituents selected from the group of bulking agents, buffering agents, tonicity modifiers, collapse temperature modifiers, solvents and/or co-solvents, solubilizing agents, preservatives, antioxidants, antimicrobial and chelating agents, wetting agents, flocculating/suspending agents, and optionally one or more proteinase inhibitors, such as selected from metallo-proteinase inhibitors, dipeptidyl-4 exopeptidase inhibitors (syn: DPP-4 inhibitors or gliptins), or hyaluronan binding protein 2 protease inhibitors, can be comprised.

According to the present invention, suitable bulking agents may comprise sucrose, lactose, trehalose, mannitol, sorbitol, glucose, raffinose, glycine, histidine or polyvinylpyrrolidone (K40). Suitable buffering agents may comprise sodium citrate, sodium phosphate, sodium hydroxide, Tris base 65, Tris acetate, or Tris HCl 65. A suitable tonicity modifier may comprise dextrose. Suitable collapse temperature modifier may be dextran, ficoll, gelatin, hydroyethyl starch. Suitable solvents are preferably selected from water for injection, and non-aqueous water miscible agents, such as ethanol, glycerin, propylene glycol and n-lactamide, may be used as co-solvents. Suitable solubilizing agents may be selected from suitable surfactants and co-solvents. Few examples of suitable surfactants are Polyoxyethylene sorbitan monooleate (Tween 80), Sorbitan monooleate, Polyoxyethylene sorbitan monolaurate (Tween 20), Lecithin, Polyoxyethylene polyoxypropylene copolymers (Pluronics). Examples of suitable co-solvents as solubilizing agents are Propylene glycol, Glycerin, Ethanol, Polyethylene glycol (300 and 400), Sorbitol, Dimethylacetamide and Cremophor EL. Suitable preservatives may be selected from parabens, such as Benzyl alcohol (0.9% to 1.5%), Methylparaben (0.18% to 0.2%), Propylparaben (0.02%), Benzalkonium chloride (0.01% to 0.02%), and Thiomersal (0.001% to 0.01%). Suitable antioxidants are preferably selected from Ascorbic acid, Sulfurous acid salts, such as Sodium bisulite, Sodium meta and bisulite, Sodium formaldehyde sulfoxylate, Thiourea, Acetylcystein, Ascorbic acid ester, butylated hydroxy toluene, tocopherols. Suitable antimicrobial agents are selected from Phenol, Meta-cresol, Benzyl alcohol, Parabens (methyl, propyl, butyl), Benzalkonium chloride, Chlorobutanol, Thimerosal, Phenylmercuric salts (acetate, borate, nitrate). Suitable chelating agents are selected from ethylene diamine tetra acetic acid salt. Suitable wetting agents are preferably selected from glycerin, alcohol and propylene glycol. Suitable flocculating/suspending agents are selected from electrolytes, such as potassium/sodium chloride, potassium/sodium citrate or potassium/sodium acetate, or surfactants and hydrophilic colloids, such as sodium carboxymethyl cellulose, acacia, gelatin, methyl cellulose, polyvinyl pyrrolidone. The proteinase inhibitors may increase the half-life of the inventive bacterial hyaluronidase and, thus, may reduce the total amount of hyaluronidase to be used or may increase the therapeutic efficacy. Edetate Calcium Disodium may be used to broadly inhibit metalloproteases. Vildagliptin or Linagliptin may be used to inhibit specifically DPP-4 exopeptidase, capable of cutting sequences with Proline. Aproptinin may be suitable to inhibit hyaluronan binding protein 2 (HABP2) and may be suitable to inhibit a broad range of serine proteases.

In case of lyophilized pharmaceutical compositions, the one or more excipients may be selected from the suitable bulking agents, buffering agents, tonicity modifiers, collapse temperature modifiers, and proteinase inhibitors. In case the inventive pharmaceutical composition is applied as a parenteral injection, the one or more pharmaceutical excipients may be selected from solvents, solubilizing agents, co-solvents, preservatives, wetting agents/surfactants, flocculating/suspending agents and proteinase inhibitors.

The respective one or more proteinase inhibitors may alternatively be administered separately to the inventive pharmaceutical composition comprising the inventive bacterial hyaluronidase. In case of separate administration, the one or more suitable proteinase inhibitors are generally administered in a suitable amount to effectively inhibit exo- and/or end-peptidases prior to or concomitantly with the inventive bacterial hyaluronidase.

In case, the inventive pharmaceutical composition including the inventive hyaluronidase is administered in form of a bolus administration followed by a subsequent unit dose administration, the protease inhibitor agents may be comprised in the bolus and optionally the subsequent unit dose of the inventive pharmaceutical composition. In order to reduce the body burden of proteinase inhibitors, preferably only the bolus administration comprises the suitable one or more protease inhibitors or the separate administration of the one or more protease inhibitors is administered prior to or concomitantly to the bolus administration of the inventive pharmaceutical composition including the inventive hyaluronidase.

As an alternative example, the liquid form of inventive pharmaceutical composition may be presented as a suspension of the inventive bacterial hyaluronidase polypeptide in a suitable suspension medium, preferably in a suitable suspension medium for parenteral application, more preferably for intravenous application. The pharmaceutical composition may be in form of a concentrate, which is to be diluted prior to parenteral application. The pharmaceutical composition for parenteral injection may comprise one or more excipients selected from the group of solubilizing agents, co-solvents, preservatives, wetting agents/surfactants, flocculating/suspending agents and proteinase inhibitors.

As an example, the liquid form of the inventive pharmaceutical composition (after dilution) for parenteral injection comprises 0.9% NaCl solution, Ringer solution, or sodium lactate-sodium chloride solution.

In general, the inventive pharmaceutical composition can be suitable for per oral, nasal, transdermal, rectal, intravenous, or intramuscular application. In case of per oral application, the inventive bacterial hyaluronidase polypeptide is preferably formulated with a suitable enteric coating to avoid/reduce degradation of the inventive bacterial hyaluronidase in enteric fluids. Particularly preferred is the intravenous application of the inventive pharmaceutical composition, as the inventive bacterial hyaluronidase polypeptide is directly, without first pass effects, present in the vascular space, which is preferably in particular for use in the treatment or prophylaxis of a hyaluronan-associated and/or proteoglycan-associated disease or disorder, preferably selected from a group consisting of homozygous familial hypercholesterolemia (xanthomatose), heterozygous familial hypercholesterolemia, or diabetic foot syndrome. In this case, the exo- and endo-peptidases may be inhibited by use of a bolus application of the inventive bacterial hyaluronidase and/or the additional administration of proteinase inhibitors in the same pharmaceutical composition or in a separate pharmaceutical composition.

A method of treating a hyaluronan-associated and/or proteoglycan-associated disease or disorder, preferably selected from a group consisting of a homozygous familial hypercholesterolemia (xanthomatose), heterozygous familial hypercholesterolemia, or diabetic foot syndrome comprising or consisting of administering the inventive modified bacterial hyaluronidase polypeptide according to the first or sixth aspect, or the inventive pharmaceutical composition seventh aspect to a subject in need thereof.

The present invention is described in the following on the basis of exemplary embodiments, which merely serve as examples and which shall not limit the scope of the present protective right.

EXAMPLES

Further characteristics and advantages of the present invention will ensue from the following description of example embodiments of the inventive aspects with reference to the accompanying drawings.

All of the features disclosed hereinafter with respect to the example embodiments and/or the accompanying figures can alone or in any sub-combination be combined with features of the aspects of the present invention including features of preferred embodiments thereof, provided the resulting feature combination is reasonable to a person skilled in the art.

Equipment (General)
1. Thermo Scientific Multifuge X3R (SN: 42343259)
2. Eppendorf Centrifuge 5920R (SN: 5948HR902433)
3. New Brunswick Scientific Innova 4300 (SN: 590544115)
4. New Brunswick Scientific Innova 4300 (SN: 791060864)
5. Jenway 6305 Spectrophotometer (SN: 68993)
6. ARCTIKO ULTF 420-80° C. Freezer (SN: 20180262153)
7. Liebherr GX 823-20M Freezer (SN: 50.636.690.7)
8. Sartorius Arium Mini UV Ultrapure Water (SN: 36802288)
9. VWR Vapour Line 135-B Autoclave (MN: 12175020)
10. Peqlab TS-100 Thermoshaker (SN: 430805037) with 24×2 ml block (SN: 191165)
11. IKA Vortex 2 S000 (SN: 100451198)
12. Fisher Scientific Mini300V Plus Power Supply (SN: 190118120)
13. IKA Rocker 2D basic Shaker (SN: 100574254)
14. Kern Precision Balance ABJ320-4NM (SN: WB18AM0063)
15. Kern PBS4200-2M Balance (SN: WB17M0023)
16. AQUALYTIC pH-Meter SD AL 10 PH (SN: AJ.12842)
17. Eppendorf 500-5000 μl pipette (SN: G44139I)
18. Eppendorf 100-1000 μl pipette (SN: J37828B)

19. Eppendorf 100-1000 μl pipette (SN: H41815D)
20. Eppendorf 10-100 μl pipette (SN: H39057D)
21. Eppendorf 10-100 μl pipette (SN: H39145D)
22. Eppendorf 0.1-10 μl pipette (SN: 400555A)
23. Bandelin Sonoplus GM 2200.2 Generator (SN: 3714.00125432.005) with Converter UW 2200 (SN: 599.00125433.006) and KE76 horn
24. Epson Workforce Pro WF-4720 (model C582A) (SN: *X2TU046376*)
25. Thermo Scientific NanoDrop Lite (SN: 5149)

Materials/Chemicals (General)
1. Glycerin (CAS: 56-81-5)
2. Agar-Agar (CAS: 9002-18-0)
3. Yeast Extract (CAS: 8013-01-2)
4. Isopropyl β-D-1-thiogalactopyranoside IPTG (CAS: 367-93-1)
5. Vegetal Peptone (CAS: 91079-46-8)
6. Sodium Chloride NaCl (CAS: 7647-14-5)
7. Potassium Chloride KCl (CAS: 7447-40-7)
8. Kanamycin solution (CAS: 25389-94-0)
9. Sodium Phosphate monobasic $NaH_2PO_4$ (CAS: 13472-35-0)
10. Sodium Phosphate dibasic $Na_2HPO_4$ (CAS: 7558-79-4)
11. Potassium Phosphate monobasic $KH_2PO_4$ (CAS: 7778-77-0)
12. Potassium Phosphate dibasic $K_2HPO_4$ (CAS: 7758-11-4)
13. Imidazole (CAS: 288-32-4)
14. d-Desthiobiotin (CAS: 533-48-2)
15. Hydrochloric Acid HCl (CAS: 7647-01-0)
16. Sodium Hydroxide NaOH (CAS: 1310-73-2)
17. Tris base (CAS: 77-86-1)
18. His GraviTrap TALON (Sigma-Aldrich GE29-0005-94)
19. StepTrap™ High Performance (Sigma-Aldrich GE28-9075-47)
20. Bovine Serum Albumin BSA (CAS: 9048-46-8)
21. Hyaluronic Acid (CAS: 9067-32-7)
22. Sodium Acetate NaOAc (CAS: 6131-90-4)
23. 2× LAEMMLI buffer (beta-mercaptoethanol CAS: 60-24-2, Sodium Dodecyl Sulfate CAS: 151-21-3)
24. Tris-MOPS SDS Running buffer (Sodium Dodecyl Sulfate CAS: 151-21-3, Tris CAS: 77-86-1, EDTA CAS: 60-00-4, MOPS CAS: 1132-61-2)
25. Methanol MeOH (CAS: 67-56-1)
26. Comassie brilliant blue R-250 (CAS: 6104-59-2)
27. Bovine Hyaluronidase Typ I-S (CAS: 37326-33-3)

1: Production of the Inventive Modified Bacterial Hyaluronidase Polypeptide of SEQ ID 1
1.1 Preparation
1.1.1 Gene Synthesis and Subcloning—pET28a(+)

The d016 gene sequence of SEQ ID No. 2 encoding the inventive modified bacterial hyaluronidase of SEQ ID No. 1 was designed by truncation of the wildtype sequence of *Streptococcus pneumonia* of SEQ ID No. 4 and the addition of C-terminal HIS-Tag gene sequence of SEQ ID No. 8 and N-terminal Strep-Tag gene sequence of SEQ ID No. 6 for a two-step affinity chromatography purification. By design, both tags were designated to remain on the final enzyme product for increased solubility and protection against (exo-) peptidases in the vascular space, which is the designated drug compartment. Synthesis of the gene construct, cloning into pET28a using NcoI/BlpI restriction sites leads to a recombinant expression vector (syn.: plasmid comprising pET28a(+) vector including d016 insert). The Vector Map Plasmid of pET28a(+) and insert d016 is displayed in FIG. 1.

1.1.2 Plasmid Transformation Into—*E. coli* BL21 (DE3)

The plasmid was transformed into host cells of *E. coli* BL21(DE3) competent cells via heat-shock at 42° C. according to supplier protocol (New England Biolabs). Selection for positive transformants of inventive host cells was performed on lysogeny broth (LB) agar plates with 50 µg/ml kanamycin antibiotics in accordance with pET28a encoded resistance. The plates were grown for 48 h at room temperature.

1.1.3 Transformant Cultivation of Inventive Host Cells in Lysogeny Broth (LB-Media and Glycerol Stock Preparation (–80° C. Storage)

A single clone of inventive host cells was picked from the plate and cultivated overnight at 37° C. in LB media with 50 µg/ml kanamycin. A sterile, pyrogen-free tube was prepared with sterilized 50% glycerol solution. Under sterile laminar flow conditions, the overnight grown liquid culture (12-14 h) was diluted in the master clone storage tube containing 50% liquid culture volume and 50% of prepared glycerol solution. The master clone was stored at –80° C. All batches of d016 inventive host cell cultivation originate from this master clone.

1.2 Production

1.2.1 Pre-Culture Inoculation in LB-Media and Overnight Growth (37° C.)

Two 250 ml culture flask (autoclaved) were prepared with (vegetal) LB media (autoclaved). 50 µg/ml kanamycin was added to prevent growth of potential bacterial contaminants. The preparation/handling of the pre-culture was conducted under sterile laminar flow conditions at all times. One flask with 65 ml of kanamycin-containing (vegetal) LB-media was inoculated by a single pipette tip (autoclaved) of sample from the master clone storage tube. A second flask was used as negative control with a pipette tip not containing cells of the master clone. The preculture tubes were sealed by an air-permeable membrane under laminar flow and delivered to the incubation shaker. Cells were grown at 37° C. overnight (12-14 h) at 180 rpm. The master clone storage tube was tightly sealed throughout the process and only opened under laminar flow conditions. After inoculation, the master clone tube was sealed and stored at –80° C.

1.2.2 Main Culture Inoculation in Terrific Broth (TB) Media, Isopropyl β-D-1-Thiogalactopyranoside (IPTG) Induced Expression Overnight (28-30° C.)

Fourteen 500 ml baffled flasks with air-permeable screwcaps were autoclaved and each was filled with 200 ml of (vegetal) TB-media (autoclaved, vegetal peptone 12 g/l, yeast extract 24 g/l, glycerol 8 ml/l) containing potassium phosphate buffer (autoclaved separately, final concentration of 9.4 g/l $K_2HPO_4$ and 2.2 g/l $KH_2PO_4$). 50 µg/ml kanamycin was added to prevent growth of potential bacterial contaminants. 12 flasks were individually inoculated by 4 ml of the preculture using 5 ml pipette tips (autoclaved). The two remaining flasks containing 4 ml of the control preculture were used as controls. The preparation of the main cultures was performed under sterile laminar flow conditions at all times. All flask caps were tightly screwed before flasks were transferred to the incubation shaker, where growth conditions were set to 37° C., 180 rpm. After 3-4 h and a growth OD600 of 0.7-1.1, all flasks were equilibrated to room temperature. Protein production was induced with 200 µl of a 100 mM IPTG stock solution. Finally, all flasks (including contamination controls) were placed inside a second incubator shaker at 28-30° C. (180 rpm) for 18-20 h.

1.2.3 Culture Harvesting and Cell Pellet Storage (–80° C.)

After the defined growth period of 18-20 h, culture flasks were taken out of the incubation shakers. Control flasks were checked to ensure that no growth of contaminants had occurred within the batch. Controls were not processed further. All twelve culture flasks were harvested using pyrogen-free, sterile 50 ml tubes. 3×50 ml of each flask were harvested and the remaining volume was discarded. All tubes were centrifuged at 4000 rcf, 4° C. for 30-45 min. The supernatant was discarded, and all tubes containing pellet comprising the inventive modified bacterial hyaluronidase were tightly sealed and stored at –80° C. for use in downstream processing.

1.3 Downstream Processing

1.3.1 Harvesting/Preprocessing: Cell Lysis by Sonication, Fragment Removal by Centrifugation Pellets were resuspended in 10 ml of the general downstream buffer PBS (phosphate buffered saline, containing 280 mM NaCl, 6 mM KCl, 15.1 mM $Na_2HPO_4$, 4.9 mM $NaH_2PO_4$, pH=7.4 at room temperature) by thorough vortexing. The three tubes of the same flask origin were combined for sonication (36 tubes were combined into 12 tubes) and stored on ice until processing. The sonicator was set to 60% amplitude, 2 sec on 4 sec off cycle. Each tube was individually sonicated, surrounded by ice-water in a 100 ml glass bottle, to ensure constant low temperatures for all samples. After sonication of all samples, the tubes were centrifuged for 45 min at 4000 rcf and 4° C. Supernatant was transferred to new sterile, pyrogen-free 50 ml tubes while ensuring that no significant amounts of cell fragment material was transferred. A further round of centrifugation for 45 min at 4000 rcf and 4° C. was performed to remove residual cell fragments. The resulting supernatant comprising the inventive modified bacterial hyaluronidase was directly used for HIS purification.

1.3.2 Purification I: HIS Affinity Chromatography, Followed by Short Term Eluate Storage (on Ice)

18 gravitational HIS-purification columns were equilibrated to general PBS downstream buffer. Contents of each centrifuged tube were distributed to 3 HIS-columns. The purification procedure was repeated twice for a single batch (2×18 columns=36 column purifications per batch). Unprocessed tubes were stored on ice at all times. Of each tube, 3×9 ml supernatant samples were carefully transferred via pipetting into 3 independent HIS-columns so as to not perturb any residual cell pellet remaining within the tube. The loaded columns were then washed by 10 ml of 10 mM imidazole PBS solution before being eluted in 6 ml 150 mM imidazole PBS solution prepared in new sterile, pyrogen-free tubes. The eluate of the 3 columns originating from the same production flask were combined (36 total purification eluates combined into 12 tubes) and diluted to 35 ml by general downstream buffer PBS. Those purified samples of the inventive modified bacterial hyaluronidase were stored on ice until the following STREP purification. The HIS-purification columns were cleaned by applying 12 ml of 300 mM imidazole PBS solution and prepared for the second run by 12 ml ultrapure water followed by 12 ml of general downstream buffer PBS.

1.3.3 Purification II: STREP Affinity Chromatography, Buffer Exchange (Tris-HCl NaCl), Short Term Eluate Storage (on Ice)

All tubes containing HIS-purified protein samples of the inventive modified bacterial hyaluronidase were stored on ice until completion of the entire STREP-purification process. For each combined eluate sample from HIS-purification, two iterations of syringe-based STREP-purification steps with a flowrate <5 ml/min were performed in each process (12 combined tubes from HIS-purification were processed by 24 STREP-columns). STREP-columns (5 ml bed volume) were washed and equilibrated by 2×25 ml general downstream buffer PBS. 17.5 ml of eluate sample was applied and run through the column. The loaded column was then washed by 50 ml of general downstream PBS buffer to remove any remaining contaminant proteins. By applying 20 ml of 2.5 mM d-Desthiobiotin containing PBS buffer, the protein of interest was eluted into a fresh, sterile and pyrogen-free tube, which was stored on ice at all times. The column was regenerated by 15 ml ultrapure water, followed by 15 ml 0.5 M NaOH, followed by 15 ml ultrapure water and finally by 25 ml of general downstream PBS buffer. At this stage, the next sample was loaded and purified in the same manner. A single STREP-column was used for 12 purification runs, i.e. half of the batch. After purification of the whole batch, buffer exchange was performed via Sartorius VivaSpin20 50 kDa centrifugal concentrators. Each VivaSpin was loaded by 20 ml of STREP-eluate. By centrifugation at 4000 rcf at 4° C. for 45 min, the samples were concentrated below 1 ml. Purified protein of the inventive modified bacterial hyaluronidase was collected in the VivaSpins and was buffer-exchanged by adding Tris-HCl NaCl (50 mM Tris, 154 mM NaCl, pH=7.4 at room temperature) to 20 ml. This procedure of centrifugal concentration and re-diluting to 20 ml by Tris-HCl NaCl was performed from that point on 3 times to meet specifications of the CoA. After the last centrifugation, the VivaSpins were not filled to 20 ml but to 5 ml. Each VivaSpin was then resuspended carefully and the 5 ml were taken out into a sterile, pyrogen-free tube. Two more resuspensions by 5 ml Tris-HCl NaCl were performed to ensure good recovery of the desired protein from the VivaSpins. All 12 tubes containing each 15 ml buffer exchanged protein of the inventive modified bacterial hyaluronidase were kept on ice for the polishing step.

1.3.4 Optional Polishing: Endotoxine (LPS Removal), Particle Removal (Filtration), Sterile Filtration, Long-Term-Storage (−15° C.)

For polishing, 2× Polymyxin B based endotoxin removal steps, 2× sterile filtration steps and 1× particle removal step were performed. In preparation, all buffer-exchanged proteins were run through sterile, pyrogen-free 0.22 μm PES filters. The filtrates were stored on ice in fresh, sterile and pyrogen-free tubes. The following steps were performed under sterile laminar flow conditions. Each sample was subject to two sequential endotoxin removal runs on (two independent) immobilized Polymyxin B columns (supplier GenScript). Each column was cleaned by a total of 15 ml of supplied regeneration buffer to remove any residual endotoxins, followed by a total of 18 ml of supplied equilibration buffer (phosphate-based) to remove all of the regeneration buffer. Additionally, a total of 15 ml of Tris-HCl NaCl was applied to further remove the phosphate buffer. The 15 ml of sterile filtered sample was loaded on the first column and gathered in a new sterile, pyrogen-free tube. To gather the remaining protein of the inventive modified bacterial hyaluronidase and enhance the yield, 5 ml of Tris-HCl/NaCl was applied to the column, and the flow-through was gathered in the same tube as well. The process was repeated using a fresh second column. Both endotoxin-removal columns were shortly regenerated multiple times within the batch run by a total of 10 ml regeneration buffer, followed by a total of 10 ml of equilibration buffer and finally followed by a total of 15 ml of Tris-HCl NaCl. A set of two endotoxin removal columns was used in total (for the whole batch). The endotoxin removal columns were regenerated after 3 sample runs. These endotoxin removal procedures were performed for all samples, and the resulting samples were stored on ice. Samples were then collected in fresh, sterile, pyrogen-free tubes and transferred under laminar flow into fresh Sartorius VivaSpin20 100 kDa centrifugal concentrators for centrifugation at 3000 rcf at 10° C. for 20 min. Under laminar flow conditions, the VivaSpin flow-through was resuspended and gathered in fresh, sterile and pyrogen-free tubes. After having gathered all the flow-through (individually for each sample), another round of sterile filtration through sterile, pyrogen-free 0.22 μm PES filters was performed inside the laminar flow. Using pyrogen-free pipette tips, a sample aliquot was made to measure the concentration of protein in the final sample via 280 nm absorption. Based on this concentration data, the combined product was diluted by Tris-HCl NaCl to a final concentration of approx. 0.1 mg/ml. Multiple small aliquots from the final product of a batch were prepared for batch analysis in sterile, pyrogen-free tubes. The final product comprising the inventive modified bacterial hyaluronidase d016 and all aliquoted batch analysis samples were tightly screwed and sealed by parafilm before storage at −15° C.

Protein yields [mg/ml] from *E. coli* BL21(DE3)/pET28a (+) shaker flask expression were determined by measuring amount of protein [mg] after HIS- & STREP purification via absorption at 280 nm (with a calculated absorption coefficient of 132590 mol-1 cm-1 and a calculated mass of 84516 Da) in reference to the culture volume [ml] during protein expression.

Thus, attained yields were approx. 0.09-0.13 mg/ml (after HIS-purification). Final yield after HIS-Purification, STREP-Purification and polishing was approx. 0.04-0.06 mg/ml.

1.4 Batch Analysis 1.4.1 Protein Purity: SDS-PAGE Analysis on Final Batch Purity by Comassie R-250 Staining For analysis of protein purity, a single batch analysis aliquot was thawed, and the concentration was checked via 280 nm absorbance. Based on this data, samples with concentrations of 0.1 μg/25 μl up to 16 μg/25 μl were created to analyze purity on the SDS-PAGE. To each dilution 25 μl 2× LAMMELI buffer was added and gently mixed by pipetting. To improve homogeneous transmission through the gel matrix, samples were then denatured by 60° C. incubation for 20 min time before loading. A following centrifugation at 20° C. and 6000 rcf for 1 min was performed to restore condensate into the sample volume. A GenScript GelBox was filled half-way with the GenScript Tris-MOPS SDS running buffer and ready-to-use SurePage gels were installed after removal of the safety strip. The inner space was then fully filled by Tris-MOPS SDS running buffer and the combs were gently removed. Each individual loading chamber (12 per gel) was washed by pipetting 100 μl of Tris-MOPS SDS multiple times to remove glycerol. All denatured and prepared samples (50 μl) were loaded (11 per gel), and an additional chamber was used to apply 5 μl of NEB Prestained Protein ladder. The GelBox was sealed and connected to the Power Supply (120 V) until the smallest band of the ladder was close to running out of the gel (60-90 min). The power was turned off, and the gel(s) were removed from the chamber. After opening the gel cassette(s), the gels were placed inside staining boxes that were filled up to 1 cm levels with staining solution (50% MeOH, 40% ultrapure water, 10% acetic acid, 1.0 g/l Comassie R-250). Gels were stained overnight on a rocker shaker. The staining solution was removed the next morning.

The gels were washed with demineralized water and heated in a microwave to est. 70-90° C. The gels were then transferred to the shaker for 20 min. The process was repeated until bands were clearly visible and the background signal had decreased significantly. As a final step, destaining scans (1200 dpi) were made (see FIG. 2) and purity was assessed based on the detection limit by monitoring visibility of sample contamination bands in 0.1 μg/lane up to 16 μg/lane samples. The detection limit was validated by a reference protein (BSA) of known quantity (0.2 μg and 0.1 μg).

Figure 2:
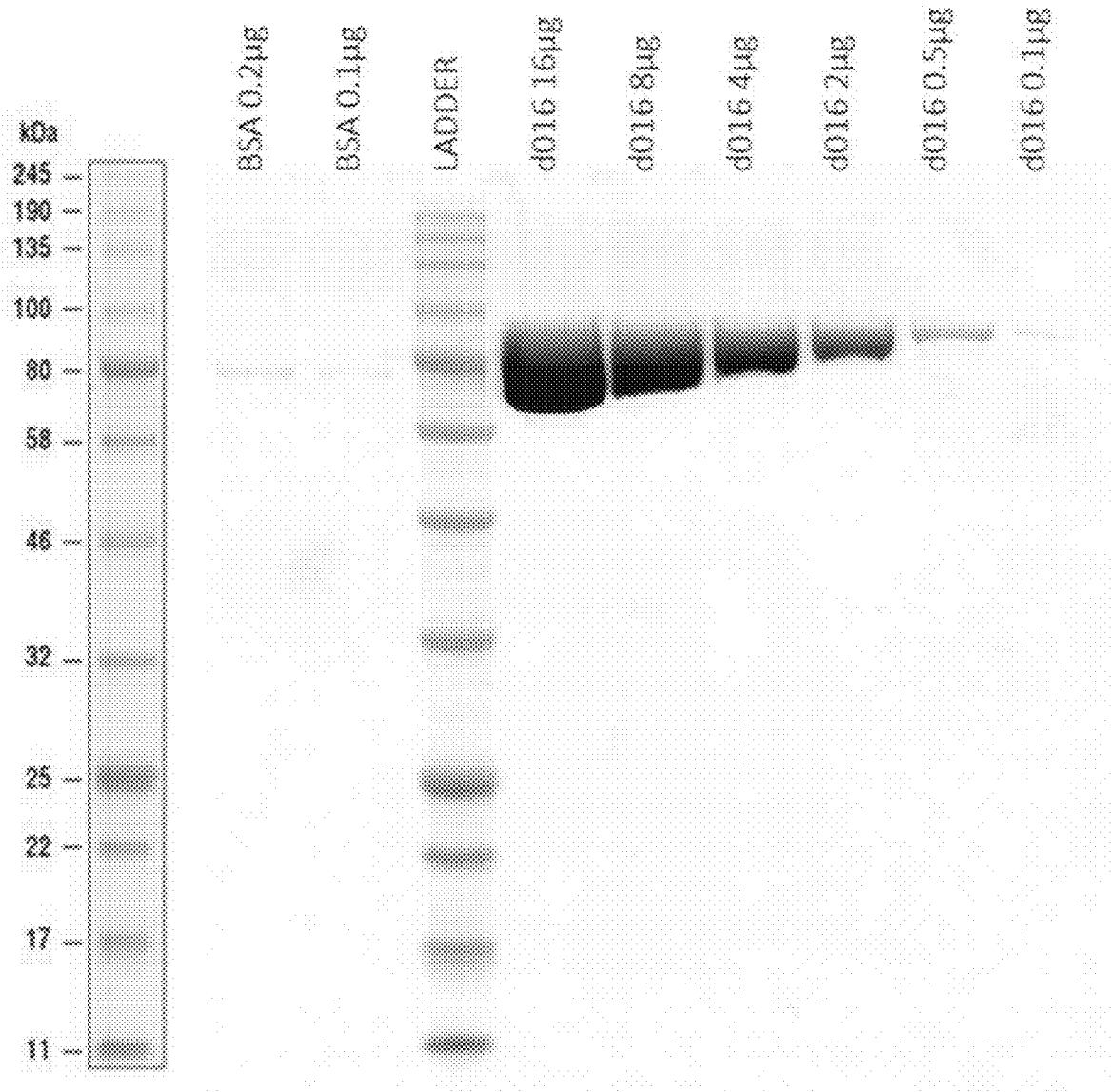
FIG. 2 represents a scan of a stained gel after SDS-Page analysis comprising reference protein (bovine serum albumin, syn: BSA) bands of different concentrations, ladder protein bands and bands of inventive modified bacterial hyaluronidase of different concentrations.

FIG. 2 represents a scan of a test batch comprising the BSA protein in concentrations 0.2 μg and 0.1 μg, ladder reference bands and the inventive modified bacterial hyaluronidase in concentrations of 16 μg, 8 μg, 4 μg, 2 μg. The protein of the inventive modified bacterial hyaluronidase migrates between the 80 kDa and 100 kDa ladder reference bands, which confirms that the inventive protein is of the correct size.

No contamination band was detectable in any of the loaded concentrations of the inventive modified bacterial hyaluronidase (0.1-16 μg), which indicates a theoretical purity of >98.8% for single contamination proteins. This finding is based on a limit-of-detection at 0.2 μg per lane, although the analyzed protein & BSA can already be detected at 0.1 μg per lane as well.

Materials:

GenScript GenBox Mini Electrophoresis tank (L00780)
NEB Prestained Protein Ladder (P7712)
GenScript SurePage Gels 10×8 12% (M00668)
Peqlab TS-100 Thermo Shaker (see equipment)
FisherScientific Mini300V Plus Power Supply (see equipment)
Thermo Fisher Scientific NanoDrop lite (see equipment)
GenScript Tris-MOPS SDS Running buffer (M00138)
Sigma-Aldrich (GE) BSA (05470)
Sigma-Aldrich LAEMMLI 2× buffer (S3401)
Eppendorf pipettes (see equipment)
Sigma-Aldrich (Nalgene) Staining box (Z358290)
Carl-Roth Methanol (KK39.2)
Sigma-Aldrich Comassie brilliant blue R-250 (27816-25G)
Epson Workforce Pro WF-4720 (see equipment)
Sartorius Arium Mini Plus (see equipment)
IKA Rocker 2D basic Shaker 1.4.2 Protein Activity: Specific Activity Measurement According to US Pharmacopoeia (USP), the unit activity of hyaluronidase is determined by calibration to the USP National Formulary Reference Standards. The unit activity was defined as: "One unit is based on the change in absorbance at 600 nm (change in turbidity) of a USP reference standard hyaluronidase which is assayed concurrently with each lot of this product."

As this standard is no longer available for purchase, supplier Sigma-Aldrich derived a method using previously calibrated reference enzymes. The new unit definition is: "One unit will cause a change in A600 nm of 0.330 per minute at pH 5.7 at 37° C. (45-minute assay)."

And furthermore: "The change in absorbance value of 0.330 in the new unit definition was chosen in order to most closely match the results found using the USP hyaluronidase standard defined activity. As a result, the discontinued USP-based unit definition and the new unit Sigma-Aldrich unit definition will give a conversion factor of approximately 1:1 (One old unit will equal approximately one new unit)." The source on the definition of activity unit is also derivable under: https://www.sigmaaldrich.com/life-science/biochemicals/biochemical-products.html?TablePage=111679355

The turbicity assay to measure activity units for the inventive modified bacterial hyaluronidase was conducted in accordance to Sigma Aldrich protocols (which includes identical preparation of all assay buffers, reaction parameters and measurement procedures). Any changed procedures are described below:

The thus described USP-based specific activity analysis was furthermore calibrated against a "reference" hyaluronidase from Sigma-Aldrich, to remove deviations arising from individual measurements. This reference enzyme (Sigma-Aldrich bovine Hyaluronidase Typ I-S [H3506]) was used in different concentrations to allow generating a standard curve (linear fit) to convert measured transmittance (blank A600—sample A600) into U/mg. Sigma-Aldrich has determined the specific activity according to the above described protocol.

The standards (3.16 U/1.5 ml reaction-6.55 U/1.5 ml reaction) were prepared by dilution procedures. To measure the specific activity, each sample of the inventive modified bacterial hyaluronidase (syn: d016) was diluted (if necessary) into Tris-HCl NaCl to a concentration of 0.1 mg/ml. Concentrations were checked by A280 measurement, and any identified deviations were used to correct the corresponding specific activity measurement.

Subsequently, the samples were diluted 400× into enzyme dilution buffer of the Sigma-Aldrich assay—11.7 μl diluted sample was used per 1.5 ml reaction, resulting in 2.93 ng d016 per 1.5 ml reaction (see Table 1 below). The dilution procedure for 2.93 ng enzyme was determined empirically to result within the absorbance of the standard range described above.

TABLE 1

| Sample (d016) | mg/ml | μg/μl | ng/μl |
|---|---|---|---|
| Concentration in Tris-HCl NaCl | 0.1 | 0.1 | |
| Concentration of 400× dilution into "Enzyme Dilution Buffer" | | 0.00025 | 0.25 |

Thus, the amount of inventive modified bacterial hyaluronidase d016 in final reaction (11.7 μl used for each reaction) corresponds to 2.93 ng/reaction.

For absorbance measurement, 250 μl of the 45 min reaction were combined with 1.25 ml precipitation buffer (pH=3.75) and measured for A600 in a spectrophotometer. This value was used to calculate transmittance and convert the value to specific activity according to aforementioned protocol.

Details on the turbicity method are described on the following website of Sigma Aldrich: https://www.sigmaaldrich.com/content/dam/sigma-aldrich/docs/Sigma/General_Information/2/hyaluronidase.pdf In reference to Sigma-Aldrich bovine Hyaluronidase, which has been determined according to USP Unit definition, the inventive modified bacterial hyaluronidase d0165 resulted in the respective specific activity as displayed in Table 2 as follows:

TABLE 2

| Sample of Test Batch | Specific Activity (USP) | Standard Deviation |
|---|---|---|
| 1 | 1.564.111 U/mg | 7% |
| 2 | 1.580.274 U/mg | 7% |

Thus, the general specific activity for the inventive modified bacterial hyaluronidase ranges between 1.5 Mio. USP U/mg+/−150k USP U/mg. This equals 25.000 katal/kg+/−2.500 katal/kg.

Materials:

Jenway 6305 Spectrophotometer (see equipment)

Sigma-Aldrich (BRAND) semi-micro UV-Cuvettes (Z628026)

Eppendorf pipettes (see equipment)

Peqlab TS-100 Thermo Shaker (see equipment)

Thermo Fisher Scientific NanoDrop lite (see equipment)

Sigma-Aldrich (Eppendorf) 3810× microtubes (Z606340)

Sigma-Aldrich (GE) BSA (05470)

Sigma-Aldrich Hyaluronic Acid (53747)

Sigma-Aldrich bovine Hyaluronidase Typ I-S (H3506)

Carl-Roth Acetic Acid (3738.2)

Carl-Roth HCl (P074.4)

Carl-Roth NaOH (9356.1)

Carl Roth Sodium Acetate (3856.1)

Carl Roth Sodium Phosphate monobasic (2370.3)

Sartorius Arium Mini Plus (see equipment)

1.4.3 Endotoxin Quantification

For Endotoxin quantification, the testing kit ToxinSensor™ Chromogenic LAL Endotoxin Assay Kit (L00350) by supplier GenScript was used in accordance with the manufacturer protocol. The kit included endotoxin standards, endotoxin-free water, Limulus Amebocyte Lysate, chromogenic substrate, color-stabilizers, endotoxin-free pipette tips and tubes, as well as a tube rack. All packaging were cleaned by ultrapure water and components were sterilized under laminar flow. The powder/lyophilized components were reconstituted and stored according to the manufacturer protocol. By diluting the endotoxin standard of the supplied kit, four standards for endotoxin measurement were prepared (0.1 EU/ml, 0.25 EU/ml, 0.5 EU/ml, 1.0 EU/ml). The standards were used to generate a reference curve, by which the absorption of each sample can be converted into a concentration in EU/ml. The respective standards were analyzed in parallel during all batch sample measurements. For batch analysis, a single batch analysis aliquot was thawed on ice, the tube was disinfected and washed by ultrapure water and transferred to laminar flow. 100 μl of an undiluted batch sample, 100 μl of endotoxin-free water as blank and four standards with endotoxin concentrations between 0.1 EU/ml and 1.0 EU/ml were used for a single analysis run. All sample handling was performed under sterile laminar flow conditions. The following steps were performed:

1. Incubation of well-mixed standards, blank and sample(s) with LAL for 12 min at 37° C.

2. Addition of substrate solution for chromogenic reaction and incubation at 37° C. for 6 min 3. Stepwise addition of the three color-stabilizer solutions to each measurement vial with gentle mixing 4. Transfer of the final reacted solutions to cuvettes for 545 nm absorption measurement on a spectrophotometer. Background from blank was subtracted from all batch sample measurements, and the standard curve was plotted. Endotoxin concentration of the sample(s) in EU/ml were extrapolated from the standard curve. By taking into account the final batch product/aliquot concentration of 0.1 mg/ml the endotoxin level was further described as EU/mg product.

1.4.4 Sterility Test

Vegetal LB-Agar (10 g/l Soya-Peptone, 10 g/l NaCl, 5 g/l Yeast Extract, 15 g/l Agar-Agar) was prepared with ultrapure water and autoclaved. The hot bottle was placed inside the ethanol-sterilized laminar flow together with sterile petri dishes. Plates were poured without addition of antibiotics to the growth media. For sterility testing, a single batch analysis aliquot was taken and thawed on ice. After the plates were solidified and cooled down, a single batch analysis aliquot was pipetted on a single plate with sterile, pyrogen-free pipette tips and spread out by sterile Lazy-L-Spreaders. A plate containing sterile filtered Tris-HCl NaCl served as control to test for environmental contaminations. A plate containing untransformed *E. coli* BL21(DE3) served as positive control. The plates were closed but not sealed to allow air exchange. To ensure environmental sterility, the plates for the product sterility test were kept inside the laminar flow for 4 days to check for any growth (timeframe may be adapted depending on environmental contamination speed during processing in laminar flow). No visible growth is confirmation for product sterility.

Figure 3A:
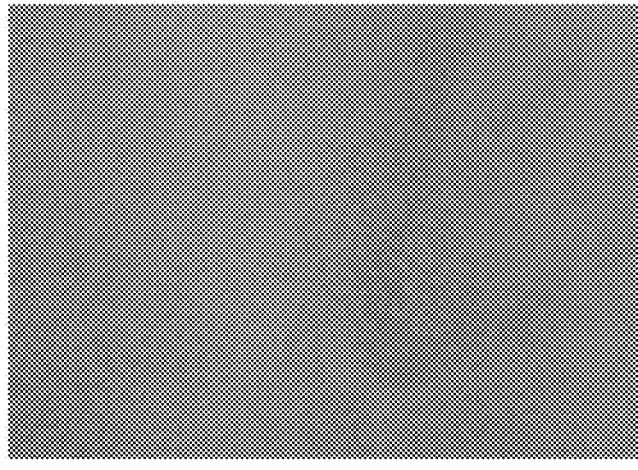
FIG. 3 represent images of LB-Agar Plates comprising *E. coli* positive control FIG. 3a), LB-plate negative control FIG. 3b) and inventive d016 sample FIG. 3c) over a time period of 4 days.
Figure 3B:
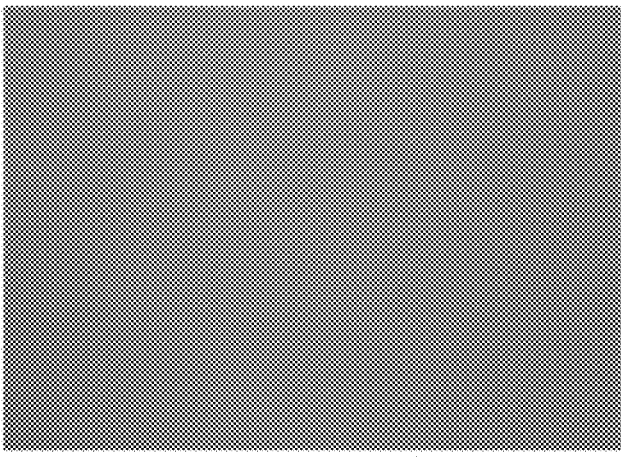
Figure 3C:
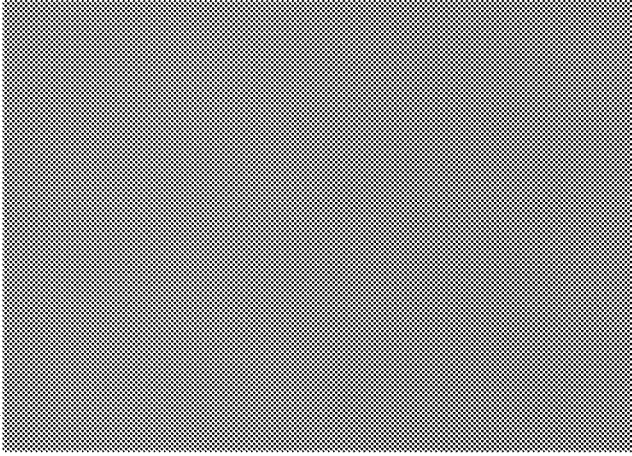

FIG. 3 show images of LB-Agar Plates comprising *E. coli* positive control FIG. 3*a*), LB-plate negative control FIG. 3*b*) and inventive d016 sample FIG. 3*c*) over a time period of 4 days. The inventive modified bacterial hyaluronidase d016 does not show any growth in antibiotic-free, vegetal LB-Agar-Plates over a time period of 4 days and, thus, is to be regarded sterile.

Accordingly, the inventive modified bacterial hyaluronidase d016 can be used for pharmaceutical compositions, in particular for pharmaceutical compositions requiring a sterile quality, such as intravenous application.

Materials:

Carl Roth vegetal Peptone (2832.2)

Carl Roth NaCl (3957.3)

Carl Roth Yeast Extract (2363.3)

Carl Roth Agar-Agar (6494.1)

Sigma Aldrich (sterile) petri dish (P5981)

Sigma-Aldrich (sterile) Lazy-L-Spreaders (Z376779)

Carl Roth (Sorenson Bioscience) pyrogen-free 1000 μl filter-tips (9773.1)

Eppendorf pipettes (see equipment)

1.4.5 Stability & Solubility, Freeze-Thaw Tests

To test stability & solubility of inventive samples, specific activity measurements of multiple concentrations of purified protein were conducted over time. Multiple sample dilutions were prepared in sterile-filtered Tris-HCl NaCl at 0.2 mg/ml (200% final stock solution of product), 0.1 mg/ml (targeted final stock solution of product) and 0.01 mg/ml (low concentration dose for targeted application). Inventive protein concentrations were measured using 280 nm absorption. Respective dilutions were stored at −15° C., 2-8° C. and 25° C. representing relevant storage and handling conditions. Aliquots for Specific Activity measurements were taken at the start of stability tests, after 1 day, 2 days, 3 days, 1 week, 2 weeks and 4 weeks. All aliquots were stored in Tris-HCl NaCl with 154 mM NaCl concentration, which equals the ionic strength of 0.9% medicinal saline solution. Aliquots were stored on ice until measurement. Measurements were performed according to the activity measurement protocol.

Furthermore, freeze-thaw tests were conducted to benchmark how product solution withstands ice crystal formation during freeze-thaw processes. Samples were frozen 5× at −80° C. and thawed again, while aliquots were taken after each cycle to measure activity. General stability & solubility results demonstrated that Specific Activity overall does not drop within 7 days if the sample concentration is above 0.1 mg/ml for −15° C., 2-8° C. and 25° C. The freeze-thaw stability of a −80° C. freeze-thaw cycle does not reduce Specific Activity if the sample is frozen less than 2 times. Sample storage concentration showed loss of protein, most likely due to adsorption, within a single freeze-thaw cycle and within a single day of storage at −15° C. and 2-8° C. of 5-15%. At 25° C. samples with a concentration above 0.2 mg/ml seem to show no concentration loss over 7 days.

The results indicate that the final product should preferably be stored in protein-low-bind tubes, at concentrations above 0.2 mg/ml and frozen not more than once to ensure absolute stability. The measurements have been conducted in small microtubes (1.5 ml) with a low filling volume of 150-1500 µl. This results in a much smaller volume-to-surface quotient, compared to product storage in 50 ml tubes. Therefore, the results above are very likely to be more dependent on adsorption effects than a commercialized product.

Materials:

Sigma-Aldrich Tris (TRIS-RO)

Carl-Roth HCl (P074.4)

Carl Roth NaCl (3957.3)

Thermo Fisher Scientific NanoDrop lite (see equipment)

Sigma-Aldrich (Eppendorf) 3810× microtubes (Z606340)

Eppendorf pipettes (see equipment)

2: Comparison of Specific Activity Between Prior Art Hyaluronidase Peptides and Inventive Modified Bacterial Hyaluronidase (Syn: D016)

2.1 Comparison of Specific Activity Between Bacterial Hyaluronidase Derived from *Streptomyces koganeiensis* (Syn: Messina Hyaluronidase) and Inventive Modified Bacterial Hyaluronidase "The rHyal_Sk in the periplasmic soluble portion was thus produced at a final concentration of approximately 2 g/L of culture medium with very high functional activity (more than 40 000 units/mg), 670- to 750-fold higher than the autologous HyaI produced by fermentation." (see Messina et al., "Identification and characterization of a bacterial hyaluronidase and its production in recombinant form", Federation of European Biochemical Societies (FEBS) Letters, Volume 590, Issue 14, July 2016, pp. 2180-2189)

Accordingly, the Specific Activity per mg for the bacterial Messina hyaluronidase derived from *Streptomyces koganeiensis* is: >40 000 U/mg, i.e. between 40 000 U/mg and 50 000 U/mg.

Specific Activity of inventive modified bacterial hyaluronidase d016 as set out in Example 1.4.2 is: 1 500 000 U/mg.

Thus, the Specific Activity of the inventive modified bacterial hyaluronidase d016 per mg protein is appr. 30× to 37.5× of the Specific Activity of the comparative Messina hyaluronidase.

2.2 Comparison of Human PH20 Hyaluronidase and Inventive Modified Bacterial Hyaluronidase d016

"The activity of Human PH20, His Tag (Cat. No. PH0-H5225) is measured by its ability to hydrolyze HA in turbidimetric assay (45 minute assay). The specific activity is >40,000 U/mg. (Unit Definition: One unit of Hyaluronidase activity will cause a change in A600 of 0.330 per minute at pH 5.35 at 37° C. in a 2.0 mL reaction mixture)"—ACRObiosystems, https://www.acrobiosystems.com/P563-Human-PH20-SPAM1-Protein-His-Tag.html Accordingly, the Specific Activity per mg for the human PH20 hyaluronidase is: >40 000 U/mg, i.e. between 40 000 U/mg and 50 000 U/mg.

Specific Activity of inventive modified bacterial hyaluronidase d016 as set out in Example 1.4.2 is: 1 500 000 U/mg.

Thus, the Specific Activity of the inventive modified bacterial hyaluronidase d016 per mg protein is appr. 30× to 37.5× of the Specific Activity of the comparative human PH20 hyaluronidase.

2.3 Comparison of Bovine Hyaluronidase and Inventive Modified Bacterial Hyaluronidase d016

"Hyaluronidase degrades hyaluronan and has been found to be inappropriately regulated during cancer progression. These enzymes randomly cleave β-N-acetylhexosamine-[1-4] glycosidic bonds in hyaluronic acid, chondroitin, and chondroitin sulfates. Unit Definition: One unit will cause a change in % transmittance at 600 nm of 0.330 per minute at pH 5.35 at 37° C. in a 2.0 mL reaction mixture (45 minute assay)."—Sigma-Aldrich, Supplier of Hyaluronidase from bovine testes Hyaluronidase from bovine testes, Type I-S, lyophilized powder 400-1 000 U/mg solid Hyaluronidase from bovine testes, Type IV-S, powder, suitable for mouse embryo cell culture 750-3 000 U/mg solid, Hyaluronidase from bovine testes, Type IV-S, lyophilized powder (essentially salt-free), 750-3 000 U/mg, Hyaluronidase from bovine testes, Type VIII, lyophilized powder, 300-1 000 U mg, Hyaluronidase from bovine testes, Type VI-S, lyophilized powder, 3 000-15 000 U/mg.

Accordingly, the Specific Activity of bovine hyaluronidases widely range between 300 and 15 000 U/mg.

Specific Activity of inventive modified bacterial hyaluronidase d016 as set out in Example 1.4.2 is: 1 500 000 U/mg.

Thus, the Specific Activity of the inventive modified bacterial hyaluronidase d016 per mg protein is appr. 100× to 5 000× of the Specific Activity of the comparative bovine hyaluronidases.

The invention claimed is:

1. A modified bacterial hyaluronidase polypeptide consisting of SEQ ID No. 1.

2. A nucleic acid encoding the modified bacterial hyaluronidase polypeptide according to claim 1, wherein the nucleic acid consists of SEQ ID No. 2.

3. A recombinant expression vector comprising an expression vector and the nucleic acid according to claim 2.

4. A host cell transformed with the recombinant expression vector according to claim 3, wherein the host cell is *E. coli*.

5. A process of production of a purified bacterial hyaluronidase polypeptide comprising the following steps:
   a. Culturing a transformed *E. coli* host cell as claimed in claim 4 in suitable growth medium under suitable conditions to express the bacterial hyaluronidase polypeptide,
   b. Harvesting the cultured transformed host cell of step a),
   c. Lysing the harvested host cell of step b) and separating resulting host cell fragments from resulting host cell content comprising the bacterial hyaluronidase polypeptide, and
   d. Purifying the resulting host cell content of step c) with histidine-tagged (HIS) affinity chromatography and streptavidin-tagged (STREP) affinity chromatography to result in a purified form of the bacterial hyaluronidase polypeptide, so that the purified hyaluronidase polypeptide consists of SEQ ID No. 1 and exhibits a purity of >98.8% and a general specific activity ranging between 1,500,000 United States Pharmacopeia Units per mg (USP U/mg)+/−150,000 USP U/mg.

6. A pharmaceutical composition comprising the modified bacterial hyaluronidase polypeptide according to claim 1 in a therapeutically effective amount and one or more pharmaceutically acceptable excipients.

7. The pharmaceutical composition according to claim 6, wherein a unit dose of the composition comprises the modified bacterial hyaluronidase polypeptide in an amount of 200 U per kg per day to 30,000 U per kg per day.

8. The pharmaceutical composition according to claim 6, wherein the composition is selected from a solid, semi-solid or liquid application form.

9. The pharmaceutical composition according to claim 6, wherein the composition is suitable for oral, nasal, transdermal, rectal, intravenous, or intramuscular application.

10. A method of treating homozygous familial hypercholesterolemia, heterozygous familial hypercholesterolemia, and/or diabetic foot syndrome comprising administering the modified bacterial hyaluronidase polypeptide according to claim 1 to a subject in need thereof.

11. A method of treating homozygous familial hypercholesterolemia, heterozygous familial hypercholesterolemia, and/or diabetic foot syndrome comprising administering the pharmaceutical composition according to claim 6 to a subject in need thereof.

* * * * *

SEQUENCE LISTING

```
<160> NUMBER OF SEQ ID NOS: 8

<210> SEQ ID NO 1
<211> LENGTH: 740
<212> TYPE: PRT
<213> ORGANISM: Streptococcus pneumoniae
<220> FEATURE:
<223> OTHER INFORMATION: Modified bacterial hyaluronidase D016

<400> SEQUENCE: 1

Met Gly Trp Ser His Pro Gln Phe Glu Lys Ala Ser Val Lys Asp Thr
1               5                   10                  15

Tyr Thr Asp Arg Leu Asp Asp Trp Asn Gly Ile Ile Ala Gly Asn Gln
```

-continued

```
                   20                25                30

Tyr Tyr Asp Ser Lys Asn Asp Gln Met Ala Lys Leu Asn Gln Glu Leu
            35                40                45

Glu Gly Lys Val Ala Asp Ser Leu Ser Ser Ile Ser Ser Gln Ala Asp
        50                55                60

Arg Ile Tyr Leu Trp Glu Lys Phe Ser Asn Tyr Lys Thr Ser Ala Asn
65                70                75                80

Leu Thr Ala Thr Tyr Arg Lys Leu Glu Glu Met Ala Lys Gln Val Thr
                85                90                95

Asn Pro Ser Ser Arg Tyr Tyr Gln Asp Glu Thr Val Val Arg Thr Val
            100               105               110

Arg Asp Ser Met Glu Trp Met His Lys His Val Tyr Asn Ser Glu Lys
            115               120               125

Ser Ile Val Gly Asn Trp Trp Asp Tyr Glu Ile Gly Thr Pro Arg Ala
            130               135               140

Ile Asn Asn Thr Leu Ser Leu Met Lys Glu Tyr Phe Ser Asp Glu Glu
145               150               155               160

Ile Lys Lys Tyr Thr Asp Val Ile Glu Lys Phe Val Pro Asp Pro Glu
                165               170               175

His Phe Arg Lys Thr Thr Asp Asn Pro Phe Lys Ala Leu Gly Gly Asn
            180               185               190

Leu Val Asp Met Gly Arg Val Lys Val Ile Ala Gly Leu Leu Arg Lys
            195               200               205

Asp Asp Gln Glu Ile Ser Ser Thr Ile Arg Ser Ile Glu Gln Val Phe
    210               215               220

Lys Leu Val Asp Gln Gly Glu Gly Phe Tyr Gln Asp Gly Ser Tyr Ile
225               230               235               240

Asp His Thr Asn Val Ala Tyr Thr Gly Ala Tyr Gly Asn Val Leu Ile
                245               250               255

Asp Gly Leu Ser Gln Leu Leu Pro Val Ile Gln Lys Thr Lys Asn Pro
            260               265               270

Ile Asp Lys Asp Lys Met Gln Thr Met Tyr His Trp Ile Asp Lys Ser
            275               280               285

Phe Ala Pro Leu Leu Val Asn Gly Glu Leu Met Asp Met Ser Arg Gly
    290               295               300

Arg Ser Ile Ser Arg Ala Asn Ser Glu Gly His Val Ala Ala Val Glu
305               310               315               320

Val Leu Arg Gly Ile His Arg Ile Ala Asp Met Ser Glu Gly Glu Thr
                325               330               335

Lys Gln Arg Leu Gln Ser Leu Val Lys Thr Ile Val Gln Ser Asp Ser
            340               345               350

Tyr Tyr Asp Val Phe Lys Asn Leu Lys Thr Tyr Lys Asp Ile Ser Leu
            355               360               365

Met Gln Ser Leu Leu Ser Asp Ala Gly Val Ala Ser Val Pro Arg Thr
    370               375               380

Ser Tyr Leu Ser Ala Phe Asn Lys Met Asp Lys Thr Ala Met Tyr Asn
385               390               395               400

Ala Glu Lys Gly Phe Gly Phe Gly Leu Ser Leu Phe Ser Ser Arg Thr
                405               410               415

Leu Asn Tyr Glu His Met Asn Lys Glu Asn Lys Arg Gly Trp Tyr Thr
            420               425               430

Ser Asp Gly Met Phe Tyr Leu Tyr Asn Gly Asp Leu Ser His Tyr Ser
            435               440               445
```

-continued

```
Asp Gly Tyr Trp Pro Thr Val Asn Pro Tyr Lys Met Pro Gly Thr Thr
    450                 455                 460

Glu Thr Asp Ala Lys Arg Ala Asp Ser Asp Thr Gly Lys Val Leu Pro
465                 470                 475                 480

Ser Ala Phe Val Gly Thr Ser Lys Leu Asp Asp Ala Asn Ala Thr Ala
                485                 490                 495

Thr Met Asp Phe Thr Asn Trp Asn Gln Thr Leu Thr Ala His Lys Ser
            500                 505                 510

Trp Phe Met Leu Lys Asp Lys Ile Ala Phe Leu Gly Ser Asn Ile Gln
        515                 520                 525

Asn Thr Ser Thr Asp Thr Ala Ala Thr Thr Ile Asp Gln Arg Lys Leu
    530                 535                 540

Glu Ser Ser Asn Pro Tyr Lys Val Tyr Val Asn Asp Lys Glu Ala Ser
545                 550                 555                 560

Leu Thr Glu Gln Glu Lys Asp Tyr Pro Glu Thr Gln Ser Gly Phe Leu
                565                 570                 575

Glu Ser Ser Asp Ser Lys Lys Asn Ile Gly Tyr Phe Phe Phe Lys Lys
            580                 585                 590

Ser Ser Ile Ser Met Ser Lys Ala Leu Gln Lys Gly Ala Trp Lys Asp
        595                 600                 605

Ile Asn Glu Gly Gln Ser Asp Lys Glu Val Glu Asn Glu Phe Leu Thr
    610                 615                 620

Ile Ser Gln Ala His Lys Gln Asn Gly Asp Ser Tyr Gly Tyr Met Leu
625                 630                 635                 640

Ile Pro Asn Val Asp Arg Ala Thr Phe Asn Gln Met Ile Lys Glu Leu
                645                 650                 655

Glu Ser Ser Leu Ile Glu Asn Asn Glu Thr Leu Gln Ser Val Tyr Asp
            660                 665                 670

Ala Lys Gln Gly Val Trp Gly Ile Val Lys Tyr Asp Asp Ser Val Ser
        675                 680                 685

Thr Ile Ser Asn Gln Phe Gln Val Leu Lys Arg Gly Val Tyr Thr Ile
    690                 695                 700

Arg Lys Glu Gly Asp Glu Tyr Lys Ile Ala Tyr Tyr Asn Pro Glu Thr
705                 710                 715                 720

Gln Glu Ser Ala Pro Asp Gln Glu Val Phe Lys Lys Leu Glu His His
                725                 730                 735

His His His His
            740
```

<210> SEQ ID NO 2
<211> LENGTH: 2251
<212> TYPE: DNA
<213> ORGANISM: Streptococcus pneumoniae
<220> FEATURE:
<223> OTHER INFORMATION: DNA Sequence encoding modified bacterial
      hyaluronidase D016

<400> SEQUENCE: 2

```
ccatgggctg gagccatccg cagtttgaaa aagcaagcgt gaaggatacg tacacggacc      60
gcttagatga ctggaacggg atcatcgcgg ggaaccagta ctatgatagc aaaaacgacc     120
aaatggcaaa attaaatcaa gaattagaag gtaaggtcgc ggattcactc tcaagcatta     180
gcagccaagc tgaccggatc tatttatggg aaaaatttag caactataaa acaagcgcca     240
accttacggc aacgtatcga aaattagagg agatggcaaa gcaggtaacg aacccgagca     300
```

-continued

```
gccgctatta tcaggatgaa acggtcgtgc ggacggtccg agattcaatg gaatggatgc      360
ataaacatgt ctacaacagc gaaaagtcaa ttgtggggaa ttggtgggat tatgaaatcg      420
gcacgccgcg cgcaatcaat aacacgttaa gccttatgaa agaatacttc agcgatgagg      480
aaattaaaaa atatacggat gtaattgaaa aatttgtccc agatccagaa catttccgga      540
agacaacgga taatccgttc aaggcgctcg gcggtaattt agtggatatg ggtcgagtca      600
aagtcatagc gggcttactt cgcaaggatg atcaggaaat tagcagcacg attcggtcaa      660
ttgagcaggt attcaagtta gtcgaccagg gcgaaggctt ttatcaggat ggttcatata      720
tcgaccacac gaacgtggca tatacaggcg cgtatgggaa cgtgttaatt gatgggttga      780
gccagctttt accggtcatt cagaagacga agaacccgat cgataaagat aaaatgcaga      840
cgatgtacca ctggattgat aaatcatttg cgccgttact tgtaaacggt gagcttatgg      900
atatgagccg cggtcggtca atcagccgcg ccaactcaga ggggcacgta gcagccgtcg      960
aagtcctccg ggggattcac cggatagctg atatgagcga aggtgaaacg aaacagcgct     1020
tacaaagctt agtaaagacg attgtgcagt cagatagcta ttatgatgtc tttaagaact     1080
taaagacgta taaggatatc agcttaatgc agtcattatt aagcgatgcc ggtgtcgcca     1140
gcgtgccgcg gacgagctac ctcagcgcat ttaataagat ggataaaacg gcaatgtaca     1200
acgccgagaa agggtttggt tttgggttaa gcttgttttc aagccgcacg ttaaactacg     1260
aacacatgaa taaggaaaac aaacgcggct ggtatacaag cgatgggatg ttctatttat     1320
acaacgggga tttaagccac tattcagatg ggtactggcc gacggtgaac ccgtataaga     1380
tgccgggcac gacggagaca gatgcgaagc gggctgattc agatacgggc aaagtgttac     1440
ccagcgcgtt cgtgggtaca tcaaaactcg atgatgcaaa cgctacggcc acgatggatt     1500
tcacgaattg gaaccagacg ttaacggcgc ataagtcatg gtttatgctc aaggataaga     1560
ttgcattttt aggttcaaac atccagaata cgagcacgga tacggcggcc acgacgattg     1620
accaacggaa acttgaaagc agcaacccgt ataaagtcta tgtcaacgat aaagaagcat     1680
cattaacgga acaggaaaag gattatccgg aaacgcagag cgggttttta gaatcatcag     1740
attcaaaaaa gaacattggc tactttttct ttaagaagag cagcatcagc atgagcaagg     1800
cgttacagaa gggtgcatgg aaggatatca acgaaggtca aagcgacaag gaagtggaaa     1860
acgaattttt aacaattagc caagcgcata agcagaacgg tgatagctat gggtatatgt     1920
tgattccgaa tgtagatcgc gcaacgttca accagatgat aaaagagtta gaatcatcat     1980
tgatcgaaaa caatgaaacg ttacaaagcg tgtatgatgc aaaacagggt gtgtggggga     2040
ttgtaaaata tgatgatagc gtcagcacga tttcaaatca gttccaggtg ttaaaacgcg     2100
gtgtctatac gattcggaaa gaaggggatg aatataagat tgcatactat aacccggaaa     2160
cgcaagaaag cgcgccggat caagaagtct ttaaaaagct cgagcatcat catcatcatc     2220
actaaccact cgacttcttt tggagctgag c                                    2251
```

<210> SEQ ID NO 3
<211> LENGTH: 949
<212> TYPE: PRT
<213> ORGANISM: Streptococcus pneumoniae
<220> FEATURE:
<223> OTHER INFORMATION: Wild Type bacterial hyaluronidase sequence

<400> SEQUENCE: 3

```
Met Val Pro Ile Glu Ala Lys Lys Lys Tyr Lys Leu Arg Phe Lys Ile
1               5                   10                  15
```

-continued

```
Lys Thr Asp Asn Lys Val Gly Ile Ala Lys Val Arg Ile Ile Glu Glu
            20                  25                  30

Ser Gly Lys Asp Lys Arg Leu Trp Asn Ser Ala Thr Thr Ser Gly Thr
            35                  40                  45

Lys Asp Trp Gln Thr Ile Glu Ala Asp Tyr Ser Pro Thr Leu Asp Val
        50                  55                  60

Asp Lys Ile Lys Leu Glu Leu Phe Tyr Glu Thr Gly Thr Gly Thr Val
65                  70                  75                  80

Ser Phe Lys Asp Ile Glu Leu Val Glu Val Ala Asp Gln Pro Ser Glu
                85                  90                  95

Asp Ser Gln Thr Asp Lys Gln Leu Glu Glu Lys Ile Asp Leu Pro Ile
            100                 105                 110

Gly Lys Lys His Val Phe Pro Leu Ala Asp Tyr Thr Tyr Lys Val Glu
            115                 120                 125

Asn Pro Asp Val Ala Ser Val Lys Asn Gly Ile Leu Glu Pro Leu Lys
        130                 135                 140

Glu Gly Thr Thr Asn Val Ile Val Ser Lys Asp Gly Lys Glu Val Lys
145                 150                 155                 160

Lys Ile Pro Leu Lys Ile Leu Ala Ser Val Lys Asp Thr Tyr Thr Asp
                165                 170                 175

Arg Leu Asp Asp Trp Asn Gly Ile Ile Ala Gly Asn Gln Tyr Tyr Asp
            180                 185                 190

Ser Lys Asn Asp Gln Met Ala Lys Leu Asn Gln Glu Leu Glu Gly Lys
        195                 200                 205

Val Ala Asp Ser Leu Ser Ser Ile Ser Ser Gln Ala Asp Arg Ile Tyr
        210                 215                 220

Leu Trp Glu Lys Phe Ser Asn Tyr Lys Thr Ser Ala Asn Leu Thr Ala
225                 230                 235                 240

Thr Tyr Arg Lys Leu Glu Glu Met Ala Lys Gln Val Thr Asn Pro Ser
                245                 250                 255

Ser Arg Tyr Tyr Gln Asp Glu Thr Val Val Arg Thr Val Arg Asp Ser
            260                 265                 270

Met Glu Trp Met His Lys His Val Tyr Asn Ser Glu Lys Ser Ile Val
            275                 280                 285

Gly Asn Trp Trp Asp Tyr Glu Ile Gly Thr Pro Arg Ala Ile Asn Asn
        290                 295                 300

Thr Leu Ser Leu Met Lys Glu Tyr Phe Ser Asp Glu Glu Ile Lys Lys
305                 310                 315                 320

Tyr Thr Asp Val Ile Glu Lys Phe Val Pro Asp Pro Glu His Phe Arg
                325                 330                 335

Lys Thr Thr Asp Asn Pro Phe Lys Ala Leu Gly Gly Asn Leu Val Asp
            340                 345                 350

Met Gly Arg Val Lys Val Ile Ala Gly Leu Leu Arg Lys Asp Asp Gln
            355                 360                 365

Glu Ile Ser Ser Thr Ile Arg Ser Ile Glu Gln Val Phe Lys Leu Val
        370                 375                 380

Asp Gln Gly Glu Gly Phe Tyr Gln Asp Gly Ser Tyr Ile Asp His Thr
385                 390                 395                 400

Asn Val Ala Tyr Thr Gly Ala Tyr Gly Asn Val Leu Ile Asp Gly Leu
                405                 410                 415

Ser Gln Leu Leu Pro Val Ile Gln Lys Thr Lys Asn Pro Ile Asp Lys
            420                 425                 430

Asp Lys Met Gln Thr Met Tyr His Trp Ile Asp Lys Ser Phe Ala Pro
```

-continued

```
                435                    440                    445
Leu Leu Val Asn Gly Glu Leu Met Asp Met Ser Arg Gly Arg Ser Ile
    450                    455                    460
Ser Arg Ala Asn Ser Glu Gly His Val Ala Ala Val Glu Val Leu Arg
465                    470                    475                    480
Gly Ile His Arg Ile Ala Asp Met Ser Glu Gly Glu Thr Lys Gln Arg
                485                    490                    495
Leu Gln Ser Leu Val Lys Thr Ile Val Gln Ser Asp Ser Tyr Tyr Asp
                500                    505                    510
Val Phe Lys Asn Leu Lys Thr Tyr Lys Asp Ile Ser Leu Met Gln Ser
                515                    520                    525
Leu Leu Ser Asp Ala Gly Val Ala Ser Val Pro Arg Thr Ser Tyr Leu
    530                    535                    540
Ser Ala Phe Asn Lys Met Asp Lys Thr Ala Met Tyr Asn Ala Glu Lys
545                    550                    555                    560
Gly Phe Gly Phe Gly Leu Ser Leu Phe Ser Ser Arg Thr Leu Asn Tyr
                565                    570                    575
Glu His Met Asn Lys Glu Asn Lys Arg Gly Trp Tyr Thr Ser Asp Gly
                580                    585                    590
Met Phe Tyr Leu Tyr Asn Gly Asp Leu Ser His Tyr Ser Asp Gly Tyr
                595                    600                    605
Trp Pro Thr Val Asn Pro Tyr Lys Met Pro Gly Thr Thr Glu Thr Asp
    610                    615                    620
Ala Lys Arg Ala Asp Ser Asp Thr Gly Lys Val Leu Pro Ser Ala Phe
625                    630                    635                    640
Val Gly Thr Ser Lys Leu Asp Asp Ala Asn Ala Thr Ala Thr Met Asp
                645                    650                    655
Phe Thr Asn Trp Asn Gln Thr Leu Thr Ala His Lys Ser Trp Phe Met
                660                    665                    670
Leu Lys Asp Lys Ile Ala Phe Leu Gly Ser Asn Ile Gln Asn Thr Ser
                675                    680                    685
Thr Asp Thr Ala Ala Thr Thr Ile Asp Gln Arg Lys Leu Glu Ser Ser
    690                    695                    700
Asn Pro Tyr Lys Val Tyr Val Asn Asp Lys Glu Ala Ser Leu Thr Glu
705                    710                    715                    720
Gln Glu Lys Asp Tyr Pro Glu Thr Gln Ser Gly Phe Leu Glu Ser Ser
                725                    730                    735
Asp Ser Lys Lys Asn Ile Gly Tyr Phe Phe Phe Lys Lys Ser Ser Ile
                740                    745                    750
Ser Met Ser Lys Ala Leu Gln Lys Gly Ala Trp Lys Asp Ile Asn Glu
                755                    760                    765
Gly Gln Ser Asp Lys Glu Val Glu Asn Glu Phe Leu Thr Ile Ser Gln
    770                    775                    780
Ala His Lys Gln Asn Gly Asp Ser Tyr Gly Tyr Met Leu Ile Pro Asn
785                    790                    795                    800
Val Asp Arg Ala Thr Phe Asn Gln Met Ile Lys Glu Leu Glu Ser Ser
                805                    810                    815
Leu Ile Glu Asn Asn Glu Thr Leu Gln Ser Val Tyr Asp Ala Lys Gln
                820                    825                    830
Gly Val Trp Gly Ile Val Lys Tyr Asp Asp Ser Val Ser Thr Ile Ser
                835                    840                    845
Asn Gln Phe Gln Val Leu Lys Arg Gly Val Tyr Thr Ile Arg Lys Glu
    850                    855                    860
```

-continued

```
Gly Asp Glu Tyr Lys Ile Ala Tyr Tyr Asn Pro Glu Thr Gln Glu Ser
865                 870             875             880

Ala Pro Asp Gln Glu Val Phe Lys Lys Leu Glu Gln Ala Ala Gln Pro
                885                 890                 895

Gln Val Gln Asn Ser Lys Glu Lys Glu Lys Ser Glu Glu Glu Lys Asn
                900                 905             910

His Ser Asp Gln Lys Asn Leu Pro Gln Thr Gly Glu Gly Gln Ser Ile
        915                 920             925

Leu Ala Ser Leu Gly Phe Leu Leu Leu Gly Ala Phe Tyr Leu Phe Arg
        930             935             940

Arg Gly Lys Asn Asn
945
```

```
<210> SEQ ID NO 4
<211> LENGTH: 2850
<212> TYPE: DNA
<213> ORGANISM: Streptococcus pneumoniae
<220> FEATURE:
<223> OTHER INFORMATION: DNA Sequence encoding Wilde Type bacterial
      hyaluronidase sequence

<400> SEQUENCE: 4
atggttccta ttgaagctaa gaaaaagtat aaactgcgtt tcaagattaa aacagataat      60
aaagtcggga ttgccaaagt tcgtatcatt gaggaaagtg gtaaggacaa gcgattgtgg     120
aattctgcaa cgacgtcagg aacaaaggac tggcagacca ttgaagcaga ctatagcccg     180
actttagatg ttgataaaat caagctggag ttattctatg aaacaggaac tgggactgtt     240
tcctttaagg atattgagct ggtagaggta gcagaccagc cttctgagga ttctcaaaca     300
gataaacaac ttgaggaaaa gattgattta ccaattggaa aaaaacatgt ttttcctctt     360
gcggactata cttataaggt agaaaatcct gacgttgctt cagtcaaaaa tggaattta     420 gaacctctta aggaagggac aaccaatgtc attgtcagta agatggcaa ggaagtgaaa     480 aagattcctt tgaagattct agcctctgtt aaggatacat acacagaccg tttggatgac     540
tggaatggca tcatcgctgg gaatcaatac tatgattcta aaaatgacca gatggccaaa     600
ttaaaccagg aattggaagg aaaggtagct gatagcctat ccagtatttc aagtcaggcg     660
gaccgcatct atttgtggga aaaattttca aattataaaa cgtctgcaaa tctgactgcc     720
acttatcgga aattggagga gatggccaag caagtgacca tccttcttc tcgttattat     780 caagatgaaa ctgtcgttcg aacagtcagg gattccatgg aatggatgca taaacatgtc     840
tacaatagtg aaaagagcat tgttgggaac tggtgggatt atgaaatcgg tacacctcgt     900
gccatcaaca ataccttgtc tctgatgaaa gaatacttct ctgatgagga aattaaaaaa     960
tatacagatg tgattgaaaa atttgtacca gatcccgaac atttccgaaa gacgactgat    1020
aacccattca aggctctagg tggaaactta gttgatatgg aagggtaaa agtaatagct    1080 ggtttactgc gtaaggatga tcaagaaatt tcttctacca ttcgctcgat tgagcaagtg    1140
ttcaagttgg tagaccaagg tgaaggtttt tatcaagatg gatcctatat cgaccacacc    1200
aatgttgcct atacgggtgc ttatgggaat gttttgattg atggcctgtc tcaactgttg    1260
ccagtcattc aaaagaccaa gaatccaatc gataaagata aaatgcaaac catgtaccac    1320
tggattgata atcgtttgc tcctttgctg gtgaatggag agctgatgga tatgagtcgt    1380
ggacgctcga tcagtcgtgc aaatagcgag gggcacgtgg ccgcagtaga agtactaaga    1440
gggattcacc gaatagcgga tatgtctgaa ggagaaacca acaacgtttt gcagagtctt    1500
```

```
gtgaagacca ttgttcaatc ggatagttat tatgatgtct ttaagaattt gaagacttat    1560
aaggatatca gtttgatgca atccttgtta agtgatgcag gagtcgcaag tgttccaaga    1620
acaagttacc tatctgcctt taacaagatg gataaaacag ccatgtacaa tgcagagaaa    1680
gggtttggat ttggcttgtc actcttttcc agtcgtacct tgaattacga acacatgaac    1740
aaggaaaata aacgtggttg gtatacgagt gatgggatgt ctatctttta caatggcgat    1800
ttgagtcact atagcgatgg ctactggcca acagttaatc catataagat gcctggtaca    1860
acagagacgg atgctaagag agcggatagc gatacaggta aagtttacc gtctgctttc     1920 gttggaacga gcaaactaga tgatgccaat gcgacagcaa ccatggatt caccaactgg     1980 aatcaaacat tgactgctca taagagctgg tttatgctaa aggataagat tgcctttta     2040 ggaagcaata tccaaaacac ttcaacagat actgctgcaa ctacaattga ccagagaaaa    2100
ctggaatcaa gtaatccata taagtctat gtcaatgata agaagcctc ccttacagaa       2160 caagaaaagg attatcctga aacccaaagt gggttttag aatcgtccga ttcgaaaaag     2220
aatattggtt acttttttctt taagaagagt tcaatcagta tgagtaaggc tttgcaaaag     2280
ggagcctgga aggatatcaa tgaaggacag tcagacaagg aagttgaaaa tgaatttctt    2340
acgattagtc aggctcataa gcaaaatgga gattcttatg gctatatgct cattcctaac    2400
gtggatcgtg ccaccttcaa tcaaatgata aaagagttag aaagcagcct catcgaaaat    2460
aacgaaaccc ttcagtctgt ttatgatgcc aaacaaggag tttggggcat tgtgaaatat    2520
gatgattctg tctctactat ttccaaccaa ttccaagttt tgaaacgtgg agtctatact    2580
attcgaaaag aaggggatga atataagatt gcctactata atcctgaaac ccaggaatca    2640
gctccagatc aggaagtctt taaaaagcta gagcaagcag ctcagccaca agtacagaat    2700
tcaaaagaaa aggaaaaatc tgaagaggaa aagaaccatt cggatcaaaa gaatctccct    2760
cagacaggag aaggtcagtc aatcttggca agtctagggt tcttgctact tggggcgttt    2820
tatttattcc gtagaggaaa gaacaactaa                                      2850
```

```
<210> SEQ ID NO 5
<211> LENGTH: 8
<212> TYPE: PRT
<213> ORGANISM: Artificial Sequence
<220> FEATURE:
<223> OTHER INFORMATION: Strep Tag Amino Acid Sequence

<400> SEQUENCE: 5

Trp Ser His Pro Gln Phe Glu Lys
1               5

<210> SEQ ID NO 6
<211> LENGTH: 24
<212> TYPE: DNA
<213> ORGANISM: Artificial Sequence
<220> FEATURE:
<223> OTHER INFORMATION: DNA Sequence encoding Strep Tag Amino Acid
      Sequence

<400> SEQUENCE: 6
tggagccatc cgcagtttga aaaa                                            24

<210> SEQ ID NO 7
<211> LENGTH: 6
<212> TYPE: PRT
<213> ORGANISM: Artificial Sequence
<220> FEATURE:
```

-continued

```
<223> OTHER INFORMATION: His Tag Amino Acid Sequence

<400> SEQUENCE: 7

His His His His His His
1               5

<210> SEQ ID NO 8
<211> LENGTH: 18
<212> TYPE: DNA
<213> ORGANISM: Artificial Sequence
<220> FEATURE:
<223> OTHER INFORMATION: DNA Sequence encoding His Tag Amino Acid
      Sequence

<400> SEQUENCE: 8
catcatcatc atcatcac                                                         18
```